United States Patent
Giordano et al.

(10) Patent No.: US 11,046,579 B2
(45) Date of Patent: Jun. 29, 2021

(54) NANOWIRE ARRAYS FOR TRACE VAPOR PRECONCENTRATION

(71) Applicant: The Government of the United States of America, as represented by the Secretary of the Navy, Arlington, VA (US)

(72) Inventors: Braden C. Giordano, Reston, VA (US); Pehr E. Pehrsson, Fairfax Station, VA (US); Kevin J. Johnson, Alexandria, VA (US); Daniel Ratchford, Alexandria, VA (US); Christopher Field, Arlington, VA (US); Junghoon Yeom, Okemos, MI (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/707,120

(22) Filed: Dec. 9, 2019

(65) Prior Publication Data
US 2020/0109049 A1 Apr. 9, 2020

Related U.S. Application Data

(63) Continuation of application No. 15/955,721, filed on Apr. 18, 2018, now Pat. No. 10,501,316, which is a
(Continued)

(51) Int. Cl.
*B82Y 10/00* (2011.01)
*H01L 29/45* (2006.01)
(Continued)

(52) U.S. Cl.
CPC ............ *B82Y 10/00* (2013.01); *B82Y 30/00* (2013.01); *G01N 27/124* (2013.01);
(Continued)

(58) Field of Classification Search
CPC ........ B82Y 10/00; B82Y 30/00; B82Y 40/00; B82Y 15/00; G01N 27/124;
(Continued)

(56) References Cited

U.S. PATENT DOCUMENTS

2008/0094051 A1* 4/2008 Williams ........... G01N 27/4146
324/76.11
2010/0176822 A1* 7/2010 Offermans .......... H01L 29/0676
324/663
(Continued)

FOREIGN PATENT DOCUMENTS

WO 2016/103561 A1 6/2016
WO 2017/047041 A1 3/2017

OTHER PUBLICATIONS

Lee et al. "MEMS Gas Preconcentrator Filled with CNT Foam for Exhaled VOC Gas Detection" Biochip J., 1 (Dec. 2014).
Search Report in EP18788159.4 (dated Nov. 11, 2020).

*Primary Examiner* — Farhana A Hoque
(74) *Attorney, Agent, or Firm* — US Naval Research Laboratory; Joseph T. Grunkemeyer

(57) ABSTRACT

Disclosed herein is a method of providing a structure having two electrodes connected by nanowires, exposing the structure to an analyte that can adsorb onto the nanowires, and passing an electrical current through the nanowires to heat the nanowires to desorb the analyte. Also disclosed herein is an apparatus having the above structure; a current source electrically connected to the electrodes, and a detector to detect the analyte.

16 Claims, 20 Drawing Sheets

Related U.S. Application Data continuation-in-part of application No. 15/049,404, filed on Feb. 22, 2016, now Pat. No. 10,167,192, which is a continuation of application No. 13/293,323, filed on Nov. 10, 2011, now Pat. No. 9,422,158.

(60) Provisional application No. 62/486,568, filed on Apr. 18, 2017, provisional application No. 61/413,664, filed on Nov. 15, 2010.

(51) Int. Cl.
| | |
|---|---|
| *G01N 27/414* | (2006.01) |
| *G01N 27/12* | (2006.01) |
| *H01L 29/06* | (2006.01) |
| *B82Y 30/00* | (2011.01) |
| *G01R 1/067* | (2006.01) |
| *B82Y 40/00* | (2011.01) |
| *B82Y 15/00* | (2011.01) |

(52) U.S. Cl.
CPC ....... *G01N 27/127* (2013.01); *G01N 27/4146* (2013.01); *H01L 29/0665* (2013.01); *H01L 29/0676* (2013.01); *H01L 29/456* (2013.01); *B82Y 15/00* (2013.01); *B82Y 40/00* (2013.01); *G01R 1/06744* (2013.01); *H01L 2924/00* (2013.01); *H01L 2924/0002* (2013.01)

(58) Field of Classification Search
CPC .............. G01N 27/4146; G01N 27/127; H01L 29/456; H01L 29/0665; H01L 29/0676; H01L 2924/0002; H01L 2924/00; G01R 1/06744
USPC ......................................................... 324/691
See application file for complete search history.

(56) References Cited

U.S. PATENT DOCUMENTS

| | | | |
|---|---|---|---|
| 2010/0244855 A1* | 9/2010 | Agache | ................ G01N 27/127 324/634 |
| 2016/0238554 A1 | 8/2016 | In et al. | |
| 2017/0212069 A1 | 7/2017 | Nakao et al. | |

\* cited by examiner

NANOWIRE ARRAYS FOR TRACE VAPOR PRECONCENTRATION

This application is a continuation application of U.S. Pat. No. 10,501,316, issued on Dec. 10, 2019, which is a continuation-in-part application of U.S. Pat. No. 10,167,192, issued on Jan. 1, 2019, which is a continuation application of U.S. Pat. No. 9,422,158, issued on Aug. 23, 2016, which claims the benefit of U.S. Provisional Application No. 61/413,664, filed on Nov. 15, 2010. U.S. Pat. No. 10,501,316 claims the benefit of U.S. Provisional Application No. 62/486,568, filed on Apr. 18, 2017. These applications and all other publications and patent documents referred to throughout this nonprovisional application are incorporated herein by reference.

TECHNICAL FIELD

The present disclosure is generally related to electrodes that may be used in sensors.

DESCRIPTION OF RELATED ART

Many types of nanowires, and other nanometer-scale structures of similar dimensions, have been at the heart of a large research effort aimed at studying their unique properties and integrating them into novel devices. For example, many different types of sensors have been fabricated from either single (Cui et al., *Science* 293 (2001) 1289) or an array of silicon nanowires (Engel et al., *Agnew. Chem. Int. Ed.* 49 (2010) 6830) to take advantage of the favorable physical, chemical, electrical, and optical properties of nanowires. For many device applications, such as gas sensors, a vertical nanowire orientation is ideal since it maximizes the surface area of nanowires that come in contact with the environment (Offermans et al., *Nano Lett.* 10 (2010) 2412), while also minimizing the deleterious effects of substrate oxides and other surface chemistry. These deleterious effects include trapping/detrapping of charge carriers, nonselective adsorption of other molecules on the substrate, and steric denial of part of the nanowire's surface to reaction with the target molecule. Furthermore, a large number of such nanowires in an array improves device performance by reducing 1/f noise and other noise types sensitive to the number of carriers.

A challenge in creating a sensor type device based on vertical nanowire arrays lies in making individual electrical connections to all the nanowires. The few existing approaches have involved embedding the entire nanowire array in some type of a sacrificial material, exposing the tips of the nanowires, and depositing the desired top contact electrode layer (Offermans et al., *Nano Lett.* 10 (2010) 2412; Park et al., *Nanotechnology* 19 (2008) 105503; Peng et al., *Appl. Phys. Lett.* 95 (2009) 243112). In these cases, the nanowire sensing region is exposed upon removal of the sacrificial material, and the substrate itself serves as the bottom electrode. Methods based on the deposition of a porous gold nanoparticle film on top of the na.nowire array (Parthangal et al., *Nanotechnology* 17 (2006) 3786) and the random gap-bridging of nanowires during growth (Ahn, et al., *Appl. Phys. Lett.* 93 (2008) 263103) have also been investigated. In all these approaches, a non-ordered array of vertical nanowires was used as the main sensing element. More importantly, none of these methods are able to create a porous top contact electrode layer with holes of controllable size and distribution.

While various methods exist for creating porous electrodes (Lohmuller et al., *J Micromech. Microeng.* 18 (2008) 115011; Kim et al., *Sens. Actuators, B* 141 (2009) 441-446), these methods are primarily designed for simply increasing the surface area of the electrode and are not applicable for creating such structures on top of a nanowire array. Other attempts, such as gold nanoparticle films (Parthangal et al., *Nanotechnology* 17 (2006) 3786) and electrospun metal nanofibers (Wu et al., *Nano Lett.* 10 (2010) 4242), do not allow precise control over the size and placement of holes in the electrode layer while also being significantly limited in the types of materials that can be used.

Accurate, reliable standoff sensing of trace vapors in complex environments, such as explosives associated with improvised explosives devices (IEDs), is both a critical need and a significant challenge. The problem is akin to that of locating the proverbial needle in a haystack: trace explosives vapors, present at concentrations several orders of magnitude below their saturated vapor concentration, must be sensed in environments containing other non-target vapors present at many orders of magnitude higher concentration.

A number of technologies have been brought to bear on this problem and can be loosely categorized as 1) spectroscopy-based, 2) sensor-based, or 3) traditional analytical approach-based. Each technology has associated pros and cons, as discussed briefly below.

Optical measurements of trace explosives vapors are intrinsically difficult in the gas phase due to the low vapor pressures associated with analytes of interest (µTorr and below, with realized vapor concentrations below ppb-levels) and the high limits of detection (LODs) attributed to these techniques. Numerous spectroscopic techniques have demonstrated capability for detecting explosives vapors, however, in many cases at concentrations that are not representative of a real world scenario (Johansson et al., "Stand-off detection of explosives vapors by Resonance enhanced Raman spectroscopy" *Proceedings of SPIE*, 8709 (2013) 87090N, 1-10; Foltynowicz et al., "Terahertz adsorption measurements for gas-phase 2,4-dinitrotoluene from 0.05 THz to 2.7 THz" *Chemical Physics Letters*, 431 (2006), 34-38; Zhang et al., "Detection of gas-phase explosive analytes using fluorescent spectroscopy of thin films of xanthene dyes" *Sensors and Actuators B: Chemical*, 225 (2016), 553-562; Todd et al., "Application of mid-infrared cavity-ringdown spectroscopy to trace explosives vapor detection using a broadly tunable (6-8 µm) optical parametric oscillator" *Applied Physics B: Lasers and Optics*, 75 (2002), 367-376). For example, resonance enhanced Raman spectroscopy has been used to detect vapors associated with nitromethane (NM) and mononitrotoluene (4-NT) at distances of 11-13 meters (Johansson). Both compounds have vapor pressures that are orders of magnitude above traditional military explosives, such as RDX and TNT, yet it was still necessary to heat the sample (NM was heated to ~55° C., and 4-NT was heated to ~100° C.) in order to enrich the surrounding air with sufficient vapor for detection. In fact, the authors note that while such an approach is functional in laboratory settings, it is difficult to implement in real scenarios due to the low concentration of vapor surrounding bulk explosives. Terahertz spectroscopy-based techniques have also been demonstrated on explosives vapors, including efforts by Foltynowicz and coworkers (Foltynowicz). They demonstrated the first gas-phase spectrum for 2,4-dinitrotoluene using pulsed terahertz time-domain spectroscopy. As with resonance enhanced Raman spectroscopy, it was necessary to heat the sample, in this case to as much as 150° C., to increase the saturated vapor pressure from 147 µTorr at room temperature to 19 Torr.

The primary spectroscopic successes are for the detection of trace particulate solids on surfaces (Bremer et al., "Standoff explosives trace detection and imaging by selective stimulated Raman scattering" *Applied Physics Letters*, 103 (2013), 061119, 1-5; Kendziora et al., "Infrared photothermal imaging for standoff detection applications" *Proceedings of SPIE*, 8373 (2012) 8373H, 1-10; Almaviva et al., "A new eye-safe UV Raman spectrometer for the remote detection of energetic materials in fingerprint concentrations: Characterization by PCA and ROC analysis" 144 (2015), 420-426; Jha et al., "Towards deep-UV surface-enhanced resonance Raman Spectroscopy f explosives: ultrasensitive, real-time reproducible detection of TNT" *Analyst*, 140 (2015), 5671-5677; Galan-Freyle et al., "Standoff detection of highly energetic materials using laser-induced thermal excitation of infrared emission" *Applied Spectroscopy*, 69 (2015), 535-544). Bremer and Dantus demonstrated laser-based standoff detection of nanograms of $HH_4NO_3$ and TNT explosives using stimulated Raman scattering (Bremer). Imaging of surfaces using this technique enabled standoff detection of particles on both textured plastic and cotton at distances up to 10 meters. Infrared photothermal imaging, in which an IR quantum cascade laser is specifically tuned to absorption bands in explosives (Kendziora), is another optical technique for detecting trace solids on a surface. The surface is imaged by an IR focal plane array, with detection occurring as a result of increases in the explosives materials temperature due to absorption of the laser light. Two obvious disadvantages of laser-based detection of trace contaminant particles are 1) the requirement that the diameters of the explosives particles on the surface are at least ~25-50 µm, suggesting a "sloppy" bomb maker, and 2) the long time needed to signal average and scan a large surface area with a laser to detect trace particle contaminants.

Chemiresistors and microcantilevers are possible chemical sensor types for trace explosives. Typical sensor development research focuses on improving either sensitivity or selectivity (Zhang et al., "Oligomer-Coated Carbon Nanotube Chemiresistive Sensors for Selective Detection of Nitroaromatic Explosives" *ACS Applied Materials & Interfaces*, 7 (2015) 7471-7475; Wang et at, "Chemiresistive response of silicon nanowires to trace vapor of nitro explosives" *Nanoscale*, 4 (2012), 2628-2632; Ray et al., "Development of graphene nanoplatelet embedded polymer microcantilever for vapour phase explosive detection applications" *Journal of Applied Physics*, 116 (2014), 124902, 1-5; Lee et al., "Direct detection and speciation of trace explosives using a nanoporous multifunction microcantilever" *Analytical Chemistry*, 86 (2014), 5077-5082), For example, Zhang and coworkers recently developed a chemiresistor based on single-wall carbon nanotubes coated with an oligomer (Zhang, *ACS Applied Materials & Interfaces*). While the sensors responded to a suite of common vapors, including acetone, ethanol, hexane, methanol, and toluene, the response was significantly greater for nitroaromatics. Their efforts demonstrated TNT detection limits of approximately 300 ppt with the addition of the oligomer, enabling them to distinguish TNT from DNT and NT when they included the response from the uncoated sensor. Despite efforts to enhance selectivity, however, chemical sensors cannot come close to matching the selectivity of traditional analytical instrumentation, e.g., mass spectrometry.

Systems-based approaches, such as commercial portable ion mobility spectrometers (IMS) are suitable for detecting trace explosives solid particulates collected on swabs, where the analyte is thermally desorbed and delivered to the IMS as a high concentration bolus of analyte. While some vapors are directly detectable via IMS, analytes such as TNT and RDX require preconcentration prior to delivery to the IMS. Martin and coworkers developed a microfabricated vapor preconcentrator coupled to a portable ion mobility spectrometer, realizing an order of magnitude improvement in sensitivity after 15 minutes of sampling (Martin et al., "Microfabricated vapor preconcentrator for portable ion mobility spectroscopy" *Sensors and Actuators B*, 126 (2007) 447-454. The single greatest challenge facing chemical sensor research is the difficulty of introducing selectivity to these microdevices sufficient to prevent significant problems associated with false negatives or false positive.

Ultimately, issues associated with selectivity and sensitivity for spectroscopic and sensor-based sensing methods mandate a focus on more traditional approaches, with an eye towards understanding the mechanisms that make these instruments so successful.

Traditional chemical detection using analytical instrumentation (i.e. gas chromatography-mass spectrometry (GC-MS)) offers robust capabilities, but at the cost of instrument size and hardware complexity. For example, current state of the art instruments incorporate vapor sampling onto a sorbent material followed by thermal desorption to a programmable temperature vaporization (PTV) inlet to focus the desorbed vapor for subsequent introduction to a GC for separation (Field et al., "Characterization of thermal desorption instrumentation with a direct liquid deposition calibration method for trace 2,4,6-trinitrotoluene quantitation" *Journal of Chromatography A*, 1227 (2012) 10-18; Field et al., "Direct liquid deposition calibration method for trace cyclotrimethylenetrinitramine using thermal desorption instrumentation" *Journal of Chromatography A*, 1282 (2013) 178-182). This methodology achieves detection at environmentally relevant levels, however, analysis time can be long (minutes to hours) due to a combination of sampling time (limited by sample flow rate through the stationary phase media) and instrument duty cycle (limited by the time necessary to desorb and refocus vapor on the PTV inlet). One modification of this approach to vapor detection is the direct delivery of materials desorbed from a reduced stationary phase volume to the head of a GC column, thus removing the PTV inlet (Giordano et al., "Dynamic Headspace-Based Generation and Quantitation of Triacetone Triperoxide Vapor" *J. Chrom. A*, 1331 (2014) 38-43. Two advantageous consequences of this modification are increased sampling flow rates and more rapid desorption due to the reduction in stationary phase volume.

The reduction in total analysis time afforded by increased sampling rate and direct desorption onto a GC column sacrifices selectivity and sensitivity, specifically measurement precision and vapor concentration at the detector. The primary reason for the degradation is the contribution of eddy diffusion to broadening of the desorbed analyte vapor cut. Eddy or multipath diffusion results from random movements as the analyte migrates through the packed sorbent bed. The resulting broadening is exacerbated by radial temperature gradients during heating of the sorbent bed. Eddy diffusion can reduce the sample concentration for a desorbed zone of analyte by several orders of magnitude, causing significant errors in elution/migration time.

BRIEF SUMMARY

Disclosed herein is a method comprising: providing a structure comprising: a first electrode; a plurality of nanowires perpendicular to the first electrode, each nanowire having a first end in contact with the first electrode; and a second electrode in contact with a second end of each nanowire; exposing the structure to a sample suspected of containing an analyte that can adsorb onto the nanowires; and passing an electrical current through the nanowires to heat the nanowires to a temperature at which the analyte will desorb from the nanowires.

Also disclosed herein is an apparatus comprising: a structure comprising: a first electrode; a plurality of nanowires perpendicular to the first electrode, each nanowire having a first end in contact with the first electrode; and a second electrode in contact with a second end of each nanowire; a current source electrically connected to the first electrode and the second electrode; and a detector configured to detect an analyte that may be desorbed from the nanowires.

BRIEF DESCRIPTION OF THE DRAWINGS

A more complete appreciation of the invention will be readily obtained by reference to the following Description of the Example Embodiments and the accompanying drawings.

FIG. 1A—bar support; FIG. 1B—close-packed monolayer of nanospheres; FIG. 1C—nanospheres with reduced diameters; FIG. 1D Au coating on the entire structure; FIG. 1E Au etch template for Si etching; FIG. 1F vertical SiNW array; FIG. 1G vertical SiNW array with the Au removed; FIG. 1H exposed tips of the SiNW array embedded in photoresist; FIG. 1I second layer of nanospheres occupying gaps in the SiNW array; FIG. 1J second layer of nanospheres with oxygen-plasma-reduced diameters; FIG. 1K Au coating on the entire structure; and FIG. 1L completed device showing the PTE and the SiNW array underneath.

FIG. 2A—close-packed monolayer of polystyrene nanospheres; FIG. 2B—nanospheres with oxygen-plasma-reduced diameters; FIG. 2C—Au etch template for Si etching; FIG. 2D—vertical SiNW array; FIG. 2E—exposed tips of the SiNW array embedded in photoresist; FIG. 2F—second layer of nanospheres perfectly occupying gaps in the SiNW array; and FIG. 2G —completed device showing the PTE and the SiNW array underneath.

FIG. 4A—1 ppm of $NH_3$, 500 ppb of $NH_3$, 1 ppm of $NO_2$, and 500 ppb of $NO_2$ at ~30% RH; and FIG. 4B—250 ppb of $NO_2$, 50 ppb of $NO_2$ and 10 ppb of $NO_2$ at <10% RH.

DETAILED DESCRIPTION OF EXAMPLE EMBODIMENTS

Figure 1A:
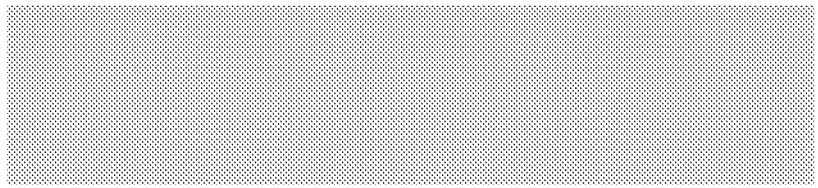
FIGS. 1A-L show schematic illustrations of cross-sectional and perspective views of the structure at various stages in the fabrication process.

In the following description, for purposes of explanation and not limitation, specific details are set forth in order to provide a thorough understanding of the present disclosure. However, it will be apparent to one skilled in the art that the present subject flatter may be practiced in other embodiments that depart from these specific details. In other instances, detailed descriptions of well-known methods and devices are omitted so as to not obscure the present disclosure with unnecessary detail.

Microfabricated sensors based on nanostructures such as spheres, wires, rods, tubes, and ribbons have been the focus of intense research in an effort to achieve field deployable, gas or liquid phase sensors for detection of chemical warfare agents and explosives. Such sensors would be selective and sensitive, miniature, low power, fast, economical, simple-to-use, and capable of detecting a wide range of analytes in complex environments such as a battlefield or an airport. The unique electrical and mechanical properties of nanostructures give them great potential but also problems in gas phase sensing platforms such as chemical field-effect transistors (ChemFETs). For example, prototype nanoscale devices are more sensitive to analyte adsorption than macroscale bulk devices because of their high surface-to-volume ratios. However, they also have relatively poor signal-to-noise ratios due to shot noise and 1/f noise, which are more significant at the nanoscale. Single nanowires can respond quickly to the analyte; however, diffusion-limited mass transport through a nanowire array prevents simultaneous response by all of the nanowires and hence increases response time. A good nanostructure-based gas sensor maximizes the surface area of the sensing element, reduces or eliminates charge carrier related noise sources, and minimizes diffusion-hindered response time.

Silicon nanowires may meet the requirements of such an ideal nanostructure-based sensor. They are easy to fabricate with existing silicon fabrication techniques that reduce cost and ensure integrability with conventional CMOS devices. Vertical arrays offer significant advantages by minimizing major noise sources at the nanoscale and maximizing sensor surface area; noisy wire-to-wire junctions are eliminated and the wire surface is not blocked by the supporting substrate. Additionally, vapor diffusion through vertically aligned silicon nanowire arrays is critical because hindered diffusion increases the response time.

Disclosed herein is a method for creating arrays of vertical nanowires, especially ordered arrays, either with a solid top electrode or a top electrode with an array of holes, especially a periodic and well-defined array of holes. The holes in the top contact electrode layer may allow various elements, such as gases or liquids, to flow rapidly through it and come in contact with the sensing nanowire region underneath. The holes or perforations may be sized and located such that electrical contact will be established to the tips of the nanowires in the array while maximizing the overall porosity of the electrode layer. In the case of the ordered arrays, the periodic placement may maximize the influx of gas or liquid from the side of the wires comprising the array. In some configurations, there may be clear channels all the way through the array. Likewise, the nanowires in an ordered array usually have similar or identical dimensions and pitch, thus minimizing wire to wire variations and allowing selection of the dimensions giving the best response. Disordered nanowire arrays may still benefit from the porous top electrode, which provides another avenue for rapid target molecule ingress to all of the nanowires comprising the array.

The support and nanowires can be any material that is compatible with the electrical measurement to be performed, including but not limited to semiconducting, conducting, metallic, or insulating material. There may be an electrical connection between the nanowires and the support. One example support material is silicon, such as a silicon wafer. The support may be a substrate or another electrode, including the perforated electrode described herein. The support may include an electrical contact on the surface opposed to the nanowires.

The nanowires may be made of the same material as the support or of a different material, and may be, for example, silicon, single-wall carbon nanotubes, multi-wall carbon nanotubes, or gallium nitride. Any material that can be made in the vertical nanowire array configuration may be used. Another option is an array of core-shell nanowires. For example, the array consists of Si nanowires that are coated with another material that is more susceptible to Joule heating than Si, so that the shell gets hot, while the Si nanowires themselves function only as a platform. The properties of the nanowire material may be either controlled or not. In the case of controlled material, this includes, for example, composition, doping and electrical conductivity, crystallinity, chemical functionalization, and additional surface layers.

There are a plurality of nanowires that are perpendicular to the support having only the second end in contact with the support. However, additional nanowires that are not perpendicular to the support may also be present. As used herein, "perpendicular" may be defined as within 1°, 5°, 10°, 20°, 40°, or 60° of normal to the support. The nanowire dimensions may be either uncontrolled or controlled as to, for example, length, diameter, and crystal face. They may be of uniform length in that they are all of a length that is within 1%, 5%, 10%, or 20% of their average length.

Methods of forming nanowires on a support are known in the art, including but not limited to methods disclosed in Huang et al., *Adv. Mater,* 23 (2011) 285-308; Kayes et al., *Appl. Phys. Lett.,* 91 (2007) 103110; Lee et al., *Nano Lett.* 10 (2010) 1016-1021; Weisse et al, *Nano Lett.* 11 (2011) 1300-1305; and Offermans et al., *Nano Lett.* 10 (2010) 2412-2415. The nanowires and support may both be made from the same precursor substrate. This may be done by etching the precursor substrate to leave behind the nanowires and the support. Other methods include, but are not limited. to, growing the nanowires on the support and attaching pre-formed nanowires to the support. Growth methods include, but are not limited to, chemical vapor deposition (catalyzed or uncatalyzed), physical vapor deposition, molecular beam epitaxy and related growth methods, and growth in a liquid.

In some embodiments, an ordered array of vertical nanowires can be etched into (Peng et al, *Adv. Mater.* 14 (2002) 1164) or grown out of (Westwater et al., *J. Vac. Sci. Technol. B* 15 (1997) 554) a substrate of various materials. The spacing between nanowires as well as their diameters can be controlled through a range of methods including, but not limited to, photolithography, electron beam lithography, interference lithography, and nanosphere lithography. A combination of nanosphere lithography and catalytic etching of silicon (Peng et al., *Appl. Phys. Lett,* 90 (2007) 163123) can quickly yield periodic vertical silicon nanowire arrays with well-controlled dimensions and material properties where every nanowire has approximately the same diameter.

The nanowires may be randomly arranged or periodically arranged on the support, such as, for example, a hexagonal arrangement of nanowires. One method to form periodic nanowires is to deposit a close-packed hexagonal array of nanospheres on a precursor substrate, etch the nanospheres to make them smaller and expose portions of the substrate between the nanospheres, deposit an etching catalyst on the nanospheres and exposed precursor substrate, removing the nanospheres, and etching the substrate. This produces a hexagonal array of nanowires of approximately equal length, of the same pitch as the close-packed array of nanospheres, and of a diameter approximately the same as the reduced-size nanospheres. Other nanoparticles may also be used to form other arrangements of nanowires. For example, nanoparticles or nanospheres ranging in size from 50 nm to 1 µm in diameter can be used, as well as larger and smaller sizes. The electrode may be made of any material that is compatible with the electrical measurement to be performed. It may be any metal or other conducting material such as a transparent conducting oxide or a film of nanotubes or other nanostructures. The electrode is of any thickness and the holes may be of any diameter and spacing. There may be an electrical connection between the nanowires and the electrode. Example electrodes may be deposited from a vapor or other method and may form a continuous material. A continuous material is formed as a single article, including a layered article, rather than as a conglomeration of smaller objects such as nanoparticles or entangled filaments. Example electrode materials include, but are not limited to, a combination of titanium and gold, silver, aluminum, graphene, and a combination of chrome and gold.

The electrode contains perforations, which are open spaces forming a straight line path normal to the support and completely through the electrode. The perforations may have a diameter that is larger than the thickness of the electrode. The perforations may be randomly arranged or periodically arranged. The nanowires described above would not have exposed tips immediately under the perforations, but additional such nanowires may be present.

One example method for forming the perforations is to deposit a filler material to cover the nanowires with a filler material leaving the first ends of the nanowires exposed. This may be done at the outset or excess filler material may be removed after completely covering the nanowires. The filler material can be any material that can later be removed without removing the nanowires and electrode, including but not limited to a photoresist, an oxide, alumina, or silica. Nanoparticles are then deposited on the filler material in the locations to become the perforations. The nanoparticles may be nanospheres in a closed-packed hexagonal array with the tips of the nanowires in the spaces between nanospheres.

Optionally, the size of the nanoparticles may be reduced to allow for smaller perforations. The electrode material is then deposited on top of the entire structure including the nanoparticles, the tips of the nanowires, and any exposed filler material. The nanoparticles and filler material along with the attached unwanted electrode material are then removed, leaving behind the substrate, nanowires, and perforated electrode.

Periodic perforations are formed when using close-packed nanospheres, which may be from a solution containing polystyrene (or similar) nanospheres spun on the sample. Spin-on parameters can be controlled to yield a close-packed monolayer of nanospheres on top of the nanowires. If the nanosphere diameter is equal to the nanowire-to-nanowire distance, each nanosphere will be geometrically constrained to fill in the gaps between the nanowires. The nanospheres will be prevented from resting on the tips of nanowires, which provides automatic alignment of additional nanospheres for particles to fill the void between wires. If the nanospheres are large enough, it will not be possible for more than one nanosphere to occupy the void between nanowires. However, smaller nanospheres or nanoparticles may be used to form multiple smaller perforations between adjacent nanowires.

The method may also be used to produce nonperiodic perforations if the nanowires are not periodic, if the nanoparticles are not closely packed, or other types of nanoparticles are used. By omitting the deposition of nanoparticles on top of the nanowires, non-perforated electrodes can be made on top of either ordered or non-ordered arrays of nanowires.

The structure may be used as a part of a sensor using a transduction mechanism for converting adsorbed molecules into an electrical signal. An electrical signal can be a change in voltage, current, resistance, frequency, or capacitance. A sensor typically sources (provides) a voltage or current and in turn measures the current or voltage, respectively. The measured value along with the output is used to convert to a resistance. The structure may be exposed to a sample, and then a change in an electrical property of the structure is measured. For example, the resistance between the support (or its included electrical contact) and the electrode may change in response to one or more analytes. Examples of the application of such sensors include the detection of gas or liquid-borne explosives and chemical or biological agents or toxic industrial chemicals (TiCs).

The following steps may be performed to form a structure.

Nanowire Formation

Figure 1B:
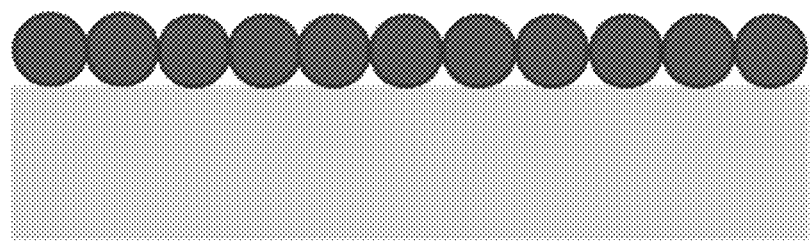
Figure 1C:
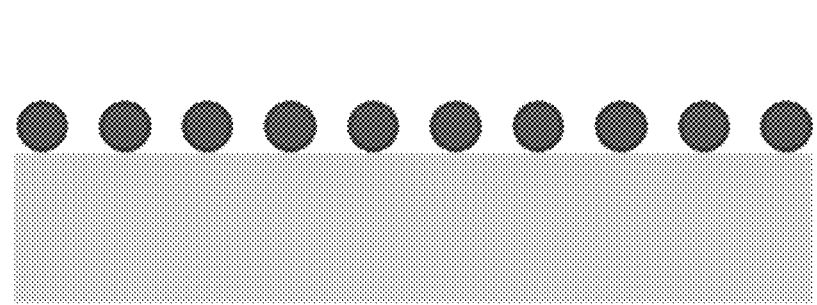
Figure 1D:
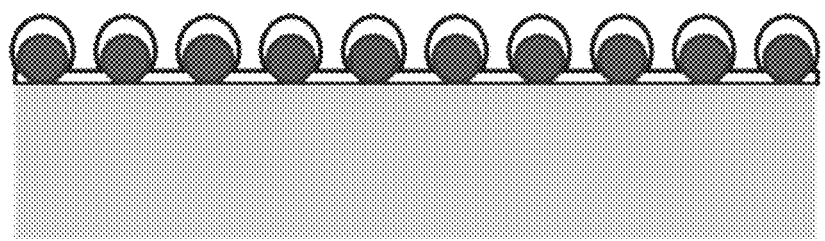
Figure 1E:
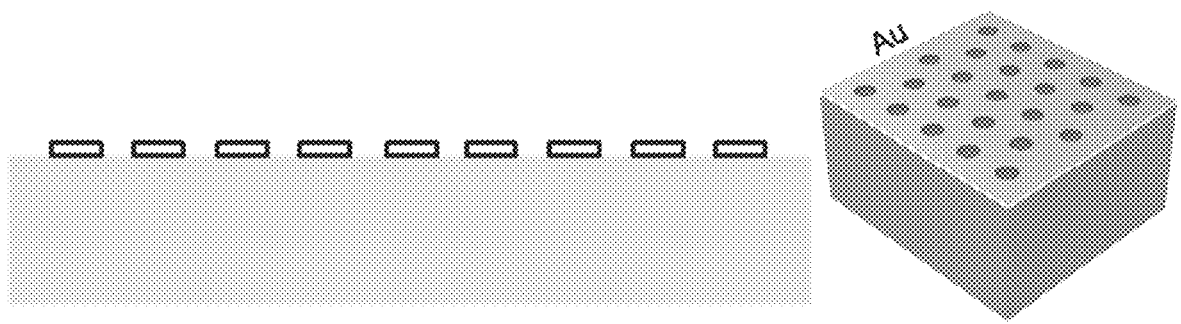
Figure 1F:
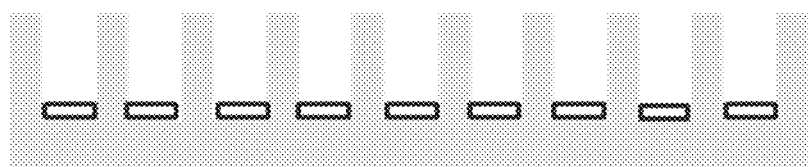
Figure 1G:
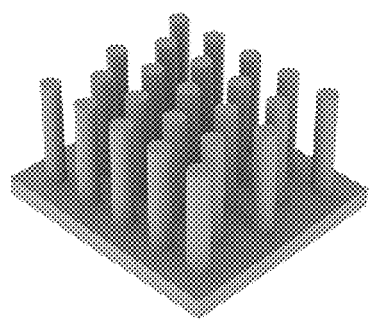

1. Start with a p-type silicon wafer with resistivity of approximately 1~10 Ω-cm.
2. Perform the following cleaning steps at room temperature (FIG. 1A):
   30 minutes in 3:1 solution of $H_2SO_4$ and 30% $H_2O_2$
   30 minutes in 5:1:1 solution of $H_2O$, $NH_4OH$, and $H_2O_2$
3. Deposit 490 nm polystyrene nanosphere solution (10% solids) on sample and spincoat to achieve close-packed monolayer (approximately 1 μL of nanosphere solution per 1 cm² of substrate) (FIG. 1B).
4. Allow sample to dry overnight.
5. Reduce nanosphere diameter to desired value using an oxygen plasma etch (FIG. 1C).
6. Deposit 25 nm of gold on top of the sample using an e-beam evaporator (FIG. 1D).
7. Remove nanospheres and unwanted metal by soaking ~5 minutes in $CHCl_3$ (FIG. 1E). Brief sonication may be necessary.
8. Etch the sample in a solution of 4.6 M HF and 0.44 M $H_2O_2$ for 20~30 minutes for nanowires around 4~8 μm in length (FIG. 1F).
9. Remove the remaining gold using a TFA gold etchant (FIG. 1G).
10. Carefully rinse and dry the sample using a critical point dryer.

Electrode Formation

Figure 1H:
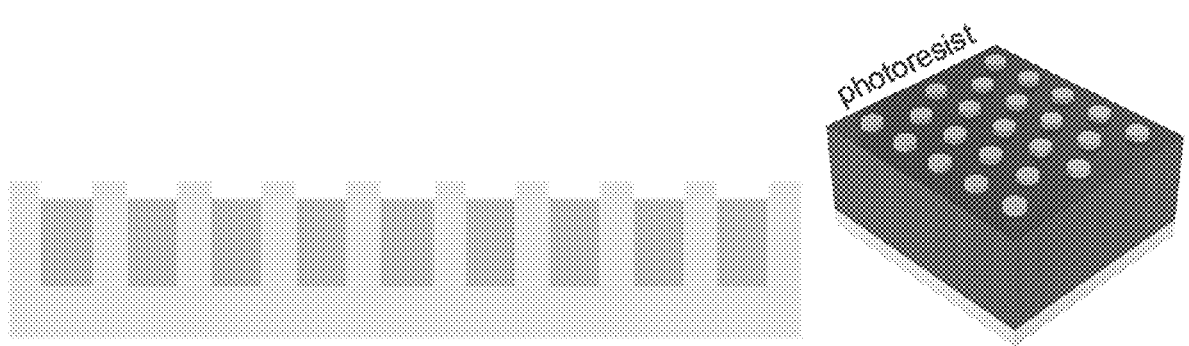
Figure 1I:
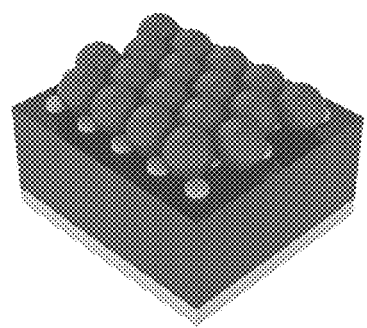
Figure 1J:
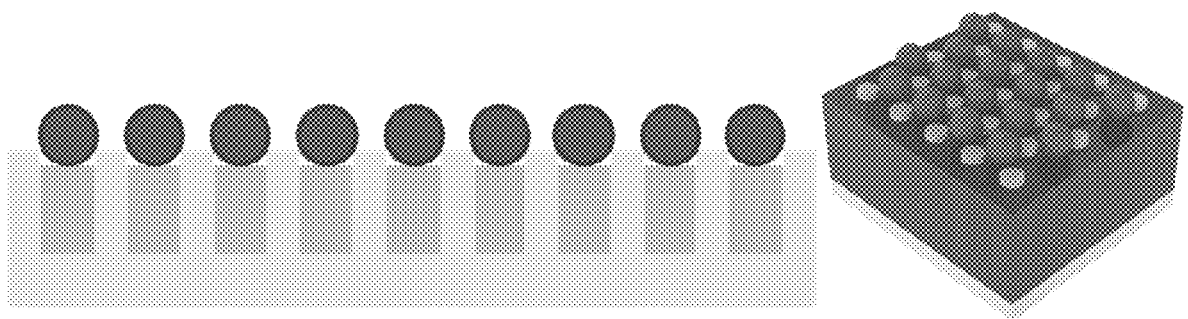
Figure 1K:
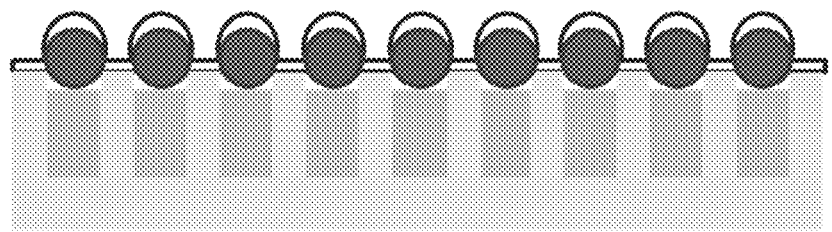
Figure 1L:
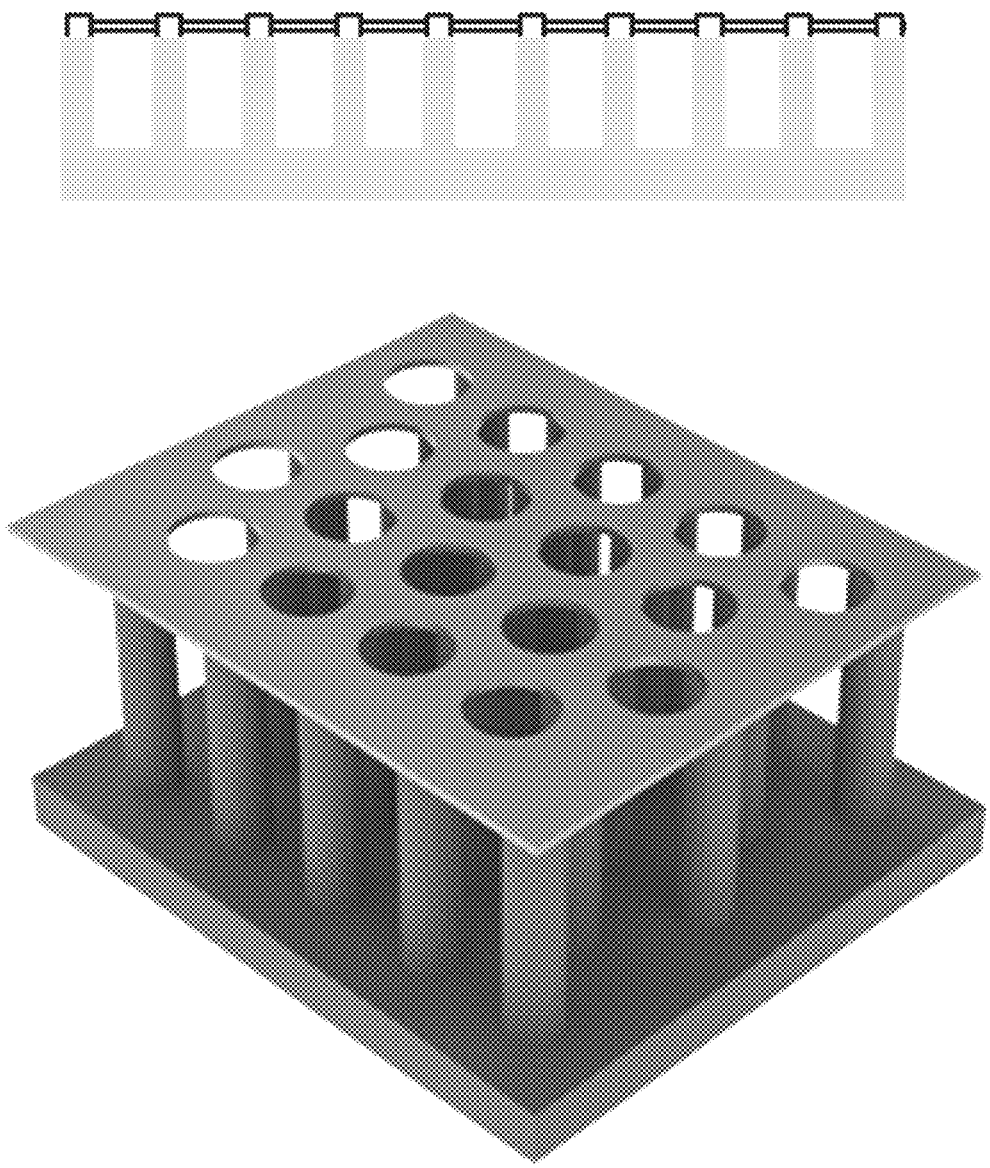

11. Deposit a thick layer of photoresist to entirely cover the nanowire array.
12. Remove the top layer of the photoresist layer using an oxygen plasma etch to reveal the nanowire tips (FIG. 1H).
13. Deposit 490 nm polystyrene nanospheres using the same process shown in step 3 (FIG. 1I).
14. Reduce nanosphere diameter to desired value using an oxygen plasma etch (FIG. 1J).
15. Deposit the electrode layer consisting of 20 nm of titanium and 100 nm of gold using an e-beam evaporator (FIG. 1K).
16. Soak the sample overnight in acetone to remove the photoresist and nanosphere layers (FIG. 1L). Brief sonication and/or soak in $CHCl_3$ may be necessary to completely remove the nanospheres.
17. Dry the sample using a critical point dryer.

In another embodiment, the nanowires are immobilized in a filler material, and then removed from the support as a unit, exposing the second ends of the nanowires. The filler material may be any material that holds the nanowires in place and can later be removed, such as a polymer or the filler materials described above. Any of the supports, substrates, nanowires, nanoparticles, electrodes, and processes described herein may be used in this embodiment.

The support may be removed from the nanowires and filler material before or after a perforated electrode is formed on the first, exposed side of the structure. In one variation, the support is removed and a perforated electrode is formed on the first side, followed by forming a second electrode on the second side. The second electrode may cover the entire second side or may be perforated by the same method as the first electrode. The second electrode may also be formed before the first. Alternatively, the first electrode is formed, then the support is removed, then the second electrode is formed. When the electrodes are formed separately, the filler material may remain present for the formation of both, or it may be removed after forming one electrode and replaced with the same or a different filler material to form the second electrode. Alternatively, the support may be removed and then both electrodes formed simultaneously.

In another embodiment, the first electrode may or may not be perforated, and the support either is a second electrode or comprises an electrical contact. Both electrodes may then be in contact with the entire array of nanowires, enabling the measurement of the electrical property through all of the nanowires.

A potential advantage of the method is the ability to form periodic perforations that are between the nanowires by an automatic process due to the self-assembly of close-packed arrays of nanospheres. No registration or alignment process is required to site the perforations. Thus, the method may be scaled to large areas including entire wafers without complications due to the size of the wafer.

Potential advantages of the structure are apparent in a gas sensor type application where the geometry-enabled gas flow through the electrode and nanowire array as well as the large number of vertical nanowires connected in parallel result in gas sensing with a fast response rate and high sensitivity. To achieve maximum gas flow throughout the structure, a perforated top electrode layer can be very effective, whether the airflow is passive or actively pumped through the sensor.

Another feature of the nanosphere-enabled perforated electrode is that the properties of the holes in the top electrode, such as pitch and diameter, can be easily controlled by simply varying the size of the nanospheres deposited atop the nanowires and changing the time for which they are etched down in oxygen plasma.

The electrodes disclosed herein can be used as a preconcentrator for detection and partial separation of trace vapors. The Si NW arrays 1) serve as high surface area adsorptive substrates for trace vapor adsorption in a noncontact/standoff mode of operation, and 2) enable rapid and controlled Joule heating profiles that provide unique thermal desorption spectra for component analysis by portable multichannel detectors (i.e., mass spectrometer or ion mobility spectrometer). By coupling the trace vapor desorption output from the Si-NW to a multichannel detector and by deconvolving the data with chemometric methodology, a correlation is established between the physical properties that determine the desorption of an analyte from an array of nanowires and the analytical properties that define its successful separation and detection within a complex, unknowable background.

The use of Si NW arrays establishes a new paradigm for tunable substrates that efficiently preconcentrate (sensitivity enhancement) and partially separate (selectivity enhancement) trace analytes in complex environments. The highly ordered silicon nanowire (Si-NW) arrays described above provide a compact, powerful front end to diverse multichannel detectors that are either currently available or in development. Differential sorption/desorption kinetics can be leveraged in a unique and powerful way to enhance selectivity while retaining instrumental simplicity, by limiting the contribution of eddy diffusion as an analyte is delivered to a detector. The arrays can 1) serve as high surface area adsorptive substrates for trace explosives vapor adsorption in a noncontact/standoff mode of operation, and 2) enable rapid and controlled Joule heating profiles that provide unique thermal desorption spectra for IED components. By coupling the trace explosives vapor desorption output to an appropriate multichannel detector (e.g. a mass spectrometer or ion mobility spectrometer) and taking advantage of chemometric methodology, one can correlate the physical properties that determine an the desorption of an analyte from a complex array of nanowires with the analytical properties that define its successful separation and detection in a complex, unknowable background.

The method can result in numerous potential advantages over existing technologies. Using the Si NW array as both a preconcentrator and separation medium reduces the overall complexity and size of traditional analytical instrumentation, and results in a significant drop in total analysis time. The form factor of the Si NW array facilitates integration with any number of multichannel or single channel detectors, for techniques including ion mobility spectrometry, mass spectrometry, optical methods, and combinations of sensor types. Joule heating of a highly ordered array minimizes eddy diffusion during the desorption process, resulting in improved sensitivity and selectivity for a given analyte. Moreover, the addition of a matrix of arrays with partially selective coatings to promote selective patterns of analyte adsorption and desorption results in 3rd order instrumentation, which is only achievable commercially in multiple hyphenated instrumentation (i.e., GC-GC-MS). The coating provides two general purposes—enhanced sensitivity and selectivity. The coating improves analyte retention on the array based upon an analytes affinity for the coating. The nature of the coating also limits retention of analytes that do not match those chemical properties, limiting adsorption and the potential for co-eluting interferents during desorption process. Generally, analyte/stationary phase interaction is governed by a number of forces including, polarity, polarizability, hydrophobicity-hydrophilicity, hydrogen bonding, and acid-base characteristics. There are many mechanisms to generate coatings with these properties including, but not limited to, liquid or vapor deposition polymerization, silanization, or adsorption. An analyte's interaction with a matrix of arrays with different coatings, in terms of preconcentration capability and retention during desorption, would be unique to the molecule of interest.

The apparatus includes a nanowire structure, a current source, and a detector. The nanowire structure is as described above and includes the plurality of na.nowires each having a first end in contact with a first electrode and a second end in contact with a second electrode. The nanowires are perpendicular to the electrodes. The nanowires may be made of any material that is warmed when current is passed through it. One suitable material is silicon.

The nanowires may include a chemically selective surface, such that not all compounds, or possibly only one compound, will adsorb onto the nanowires. Suitable surfaces include, but are not limited to, an adsorbing layer, a stationary phase such as is used in a chromatograph, and a surface functionalization, which can range from the sub-monolayer to materials that completely fill the interwire spaces. For example, a ruthenia coating ($RuO_x$) may be used for detecting carbon monoxide. Functional groups may be added to silicon using compounds containing the functional group and alkoxy silane groups. Such functional groups include, but are not limited to, hexafluoroisopropanyl to detect nitro groups, pyrrole and thiophene to detect π-electron acceptors, and carboxylic acid to detect organic bases.

An electrode may have perforations as described above. It may be a continuous material and may be made from titanium and gold or other suitable metals and metal combinations with appropriate chemical reactivity and electrical conductivity. The current source is electrically connected to the electrodes so that a current may be passed through the nanowires.

The apparatus may include more than one of the structures. The multiple structures may include structures having different chemically selective surfaces.

The detector may be any detector capable of detecting the analyte vapor. Suitable detectors includes, but are not limited to, a mass spectrograph, an ion mobility spectrograph, a fluorescent probe, a cantilever, a chemiresistor, or a nanowire array as disclosed herein. The apparatus may also include a gas chromatograph for separating vapors from the preconcentrator before they are detected.

The apparatus may be used by exposing the nanowire structure(s) to a sample, such as ambient air, that is suspected of containing an analyte, such as an explosive vapor. The analyte adsorbs onto the nanowires. A period of time is allowed to pass to increase the amount of analyte that is adsorbed. Then the current source passes a current through the nanowires, which causes them to warm up by Joule heating. When the nanowire temperature is high enough, any adsorbed analyte desorbs into a vapor that may be more concentrated than the original sample. The analyte may then optionally pass through a gas chromatograph, and then pass to the detector.

The following examples are given to illustrate specific applications. These specific examples are not intended to limit the scope of the disclosure in this application.

Figure 2A:
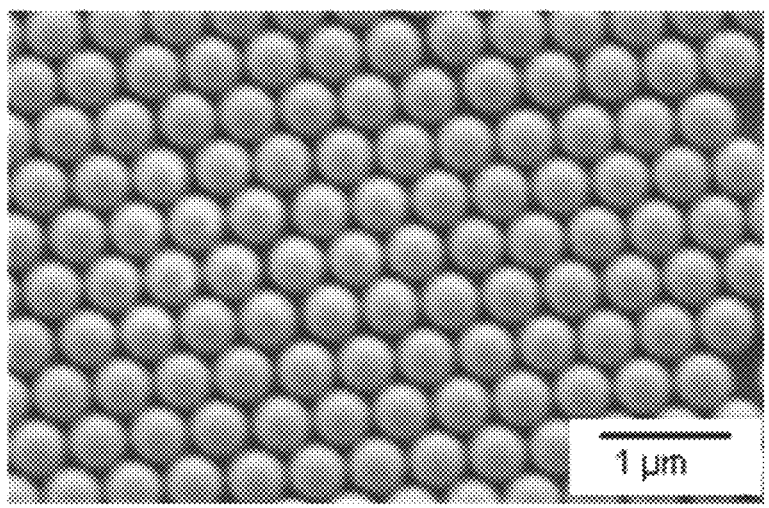
FIGS. 2A-G show scanning electron microscope (SEM) images of the structure at various stages in the fabrication process.
Figure 2B:
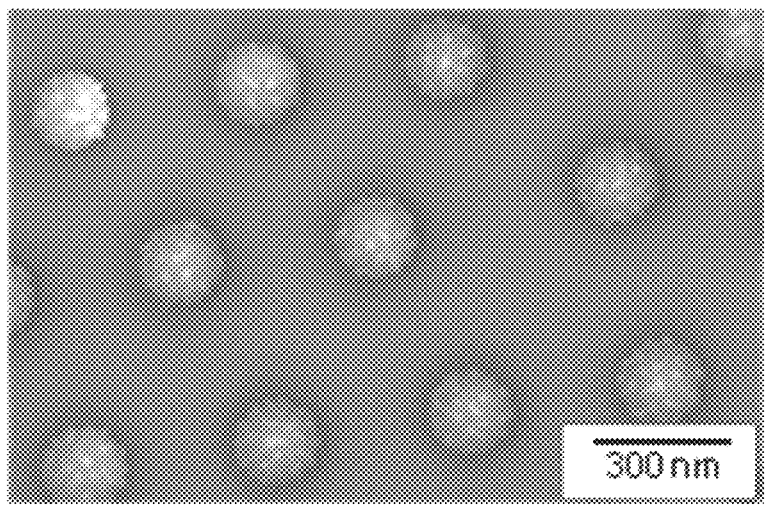
Figure 2C:
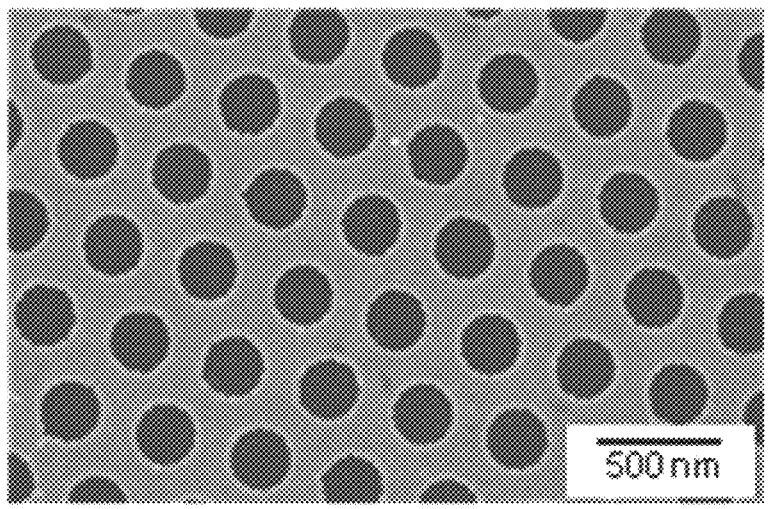
Figure 2D:
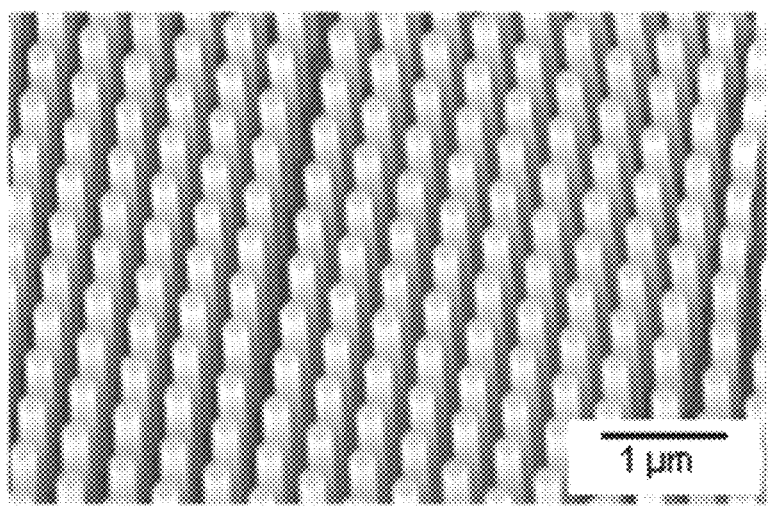
Figure 2E:
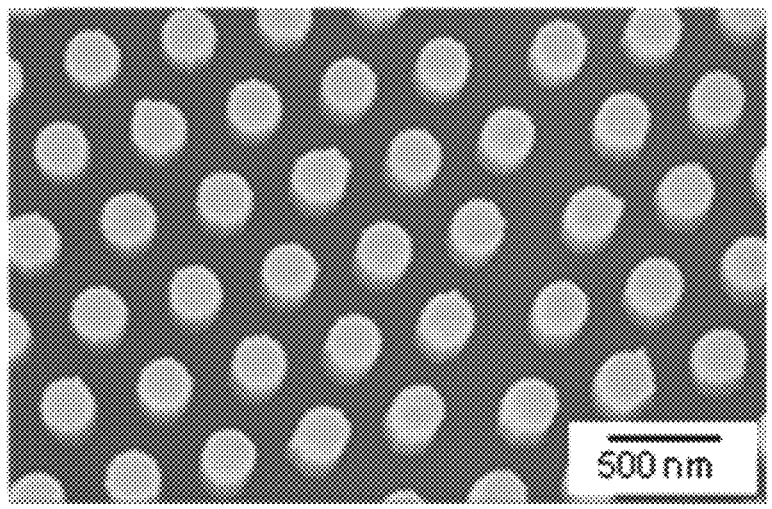
Figure 2F:
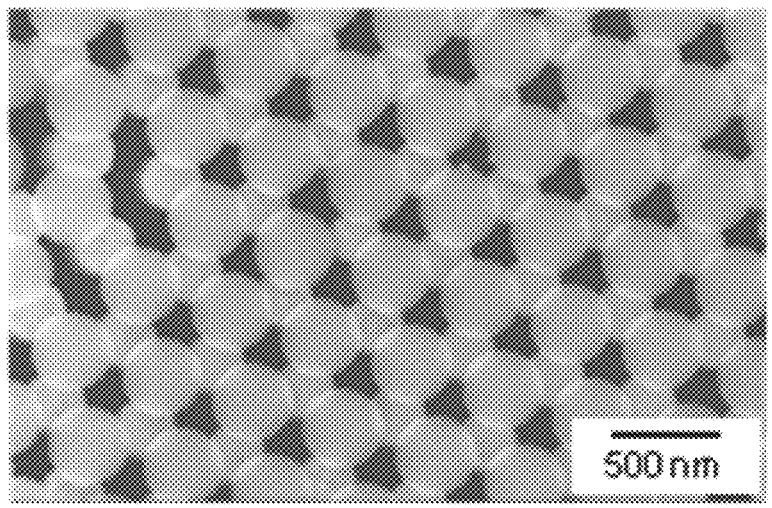
Figure 3:
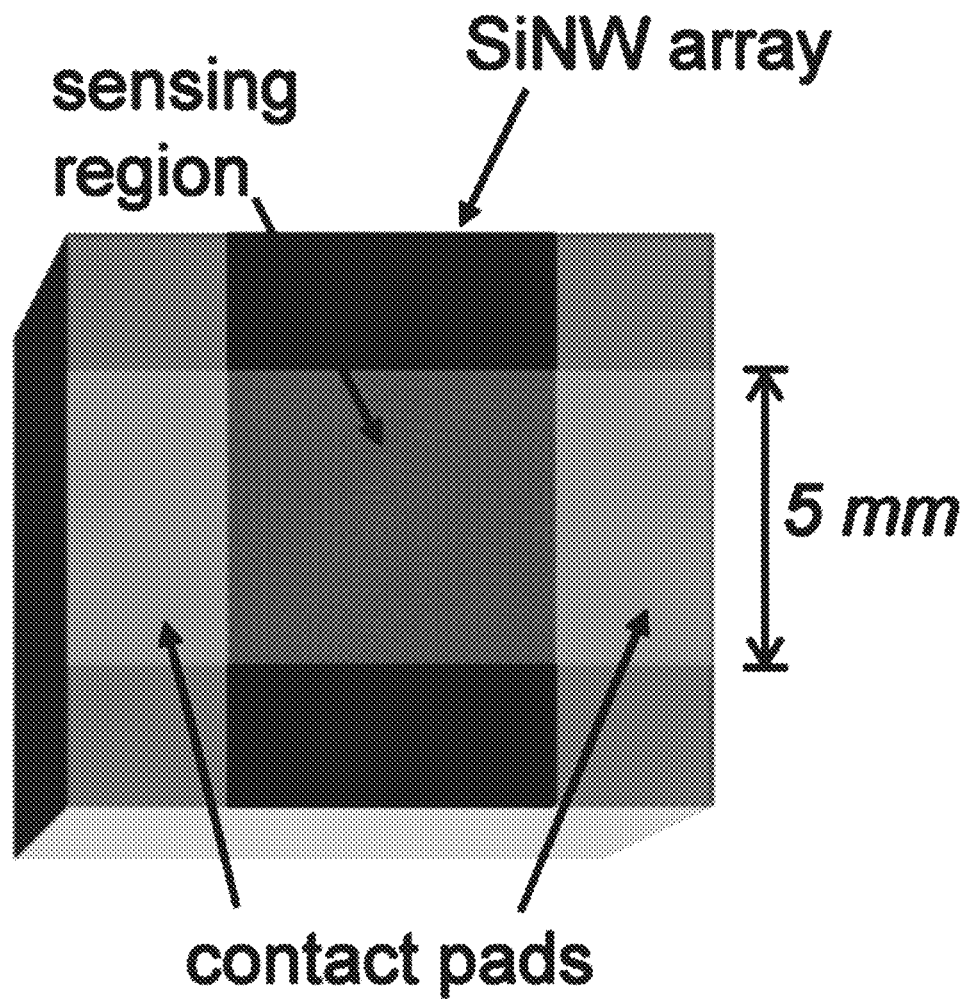
FIG. 3 shows a schematic diagram of completed device (top view).

In one study, a combination of na.nosphere lithography and metal-assisted chemical etching was used to synthesize well-ordered arrays of silicon nanowires (SiNWs) (Peng. et al., *Appl. Phys. Lett.*, 95 (2009) 243112). Silicon was chosen for its ease of fabrication and integration as well as the wide availability of various functionalization and surface modification techniques for increased sensitivity and selectivity. Precise control over dopant type and concentration is available in commercially obtained wafers. The process started with a 100 mm diameter B-doped p-type Si(100) wafer of resistivity ~10 Ω·cm that was cut into 1 cm² pieces and successively cleaned in a 3:1 solution of $H_2SO_4:H_2O_2$ (30%), 1:1:5 solution of $H_2O_2(30\%):NH_4OH:H_2O$ and deionized water. The resulting hydrophilic substrate was then spin-coated (Cheung et al., *Nanotechnology* 17 (2006) 1339-43) (FIG. 2A) with a close-packed monolayer of 490 nm polystyrene nanospheres (Bangs Laboratories, 10% w/v). The nanospheres were subsequently reduced in diameter via an oxygen plasma etch (FIG. 2B). A perforated gold template for the catalytic anisotropic etching of silicon was created by evaporating a 25 nm thick layer of gold on top of the nanosphere array and subsequently removing the nanospheres by soaking in $CHCl_3$ (FIG. 2C). The SiNWs were then formed by immersing the device in a solution of 10% HF and 0.6% $H_2O_2$, where gold selectively and anisotropically etched into the silicon substrate, leaving behind a well-ordered array of vertically standing nanowires (FIG. 2D. A photoresist layer could be patterned over parts of the template to prevent the etching of silicon in certain locations, such as the contact pad region (FIG. 3). The silicon etch rate in the $HF-H_2O_2$ solution depends on multiple factors, including solution concentration, temperature, template dimensions, etc., but was shown to be approximately 200 nm min$^{-1}$ in this case. The samples were typically etched for around 30 min to create up to ~4×10⁸/ cm² vertical SiNWs that were 4-6 μm in length and ~200 nm in diameter, with a nanowire-to-nanowire distance of 490 nm. The initial diameter of the polystyrene nanospheres defined the SiNW array's period while the combination of this initial diameter and subsequent etching of the nanospheres in oxygen plasma defined the resulting nanowire diameter. Next, a 500 nm thick layer of $SiO_2$ was evaporated over the entire device to electrically isolate the contact pad region from the bulk of the substrate. The oxide layer was then selectively etched away to reveal the SiNW array while removing any residual oxides on the nanowire surfaces. This step also decreased the contact resistance and established ohmic contact between the nanowire tips and the electrode layer deposited later. The entire SiNW array was then covered with a thick photoresist that was subsequently etched back in oxygen plasma to reveal just the SiNW tips (FIG. 2E).

Figure 2G:
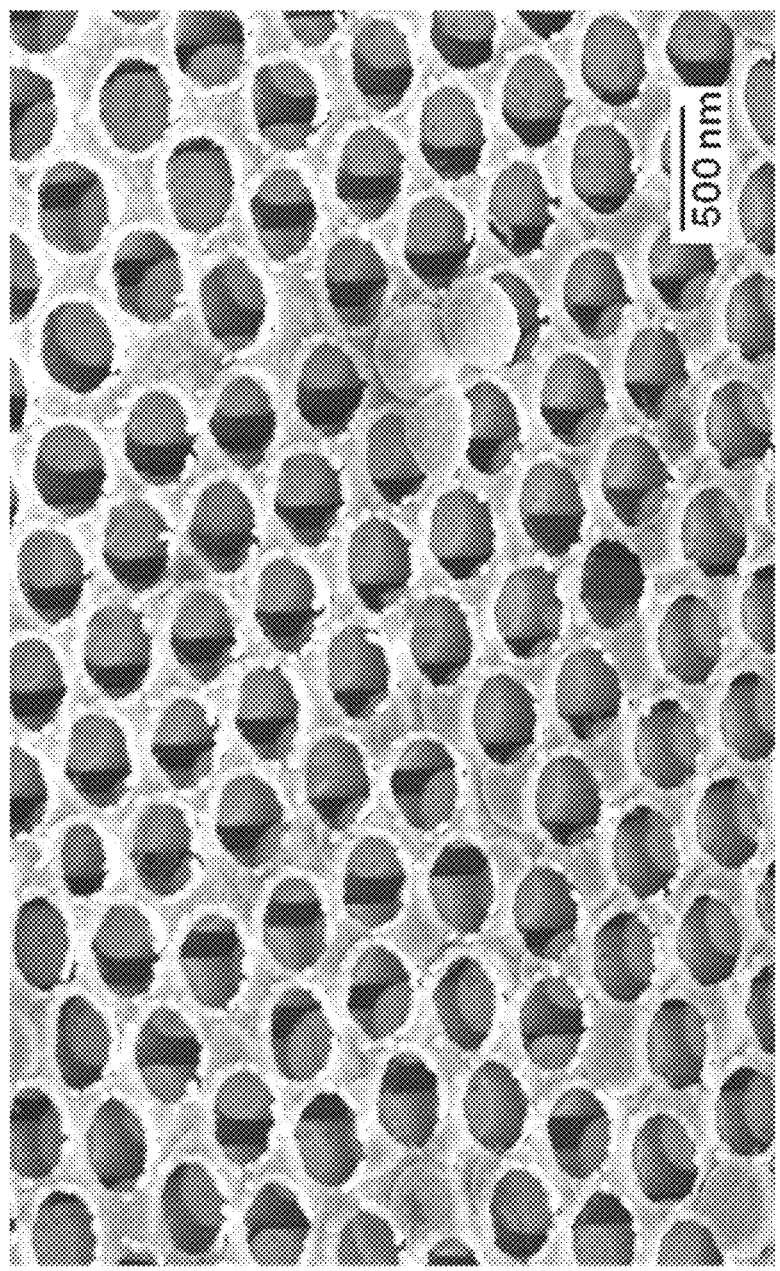

After exposing the SiNW tips, a second layer of nanospheres identical to the ones used earlier in making the etch template was deposited. Since the period of this second nanosphere layer was equal to the period of the SiNWs, the new nanospheres were physically constrained to perfectly occupy the voids in the array and form a close-packed array on top of the exposed SiNW tips. After slightly etching down the second nanosphere array in an oxygen plasma , evaporating a metal electrode layer consisting of 20 nm thick titanium and 100 nm thick gold, and finally removing the photoresist and nanospheres with acetone, a large SiNW array (5 mm×5 mm) with a PTE layer was formed as seen in FIG. 2G. Some polystyrene nanospheres are still visible in and are the result of local variations in photoresist and gold film thickness. The size and distribution of pores could be controlled by varying the nanosphere processing conditions, and the contact resistance between the nanowires and the top electrode could be reduced even further by performing a low-temperature anneal. The completed devices were mounted on pin grid array (PGA) packages using a conductive epoxy to make the bottom electrical connections. Top electrical connections were made by wirebonding to the contact pads (FIG. 3).

To evaluate the chem/biosensing capabilities of the PTE SiNW array sensors, the completed devices were exposed to varying levels of $NO_2$ or $NH_3$ in a custom-built testing chamber (Field et al., *Anal. Chem.* 83 (2011) 4724-4728). A dual manifold (an analyte line and a clean air line) was constructed out of coated stainless steel (SilcoNert Coated Stainless Steel Tubing, Restek) to minimize wall adsorption. Compressed gas cylinders of ammonia and nitrogen dioxide were connected to the analyte line of the manifold. A zero air generator (Environics) and humidity control unit (Miller-Nelson) were used to create humidified air (~40% relative humidity) for both the analyte and clean air lines of the manifold. The known concentrations of the analyte were achieved by diluting calibrated gas standards (100 ppm ammonia and 50 ppm nitrogen dioxide, Airgas) with the carrier air via a T-connector and mass flow controller. A three-way valve and actuator were used to switch between the clean and analyte lines of the manifold. The entire manifold was placed in a temperature controlled oven. A stainless steel sample chamber with a cone geometry was built for testing PGA-mounted sensors. A sample pump was used to flow air through the chamber at 100 mL/min.

Electrical connections within the sample chamber were made with a zero-insertion force (ZIF) socket and a simple printed circuit board for easy loading and unloading of sensors. A multiplexer (Keithley, 2001) and source-meter (Keithley, 2602) were connected to the circuit board of the sample chamber. The multiplexer allowed for selection of specific pins and functions of the PGA and sensor, respectively. Resistance was monitored by sourcing 100 μA of current and recording the voltage at a sample rate of 10 Hz. The sensor electronics were monitored and controlled by a Lab VIEW program. The resistance recorded during exposure to clean air was averaged to obtain the initial resistance, $R_0$. The sensor response ($\Delta R/R_0$) was calculated as the difference in resistance (R-$R_0$, $\Delta R$) normalized by the initial resistance ($R_0$) for comparison and further evaluation. All data modeling and plotting were performed using the OriginPro 8.1 software package.

Without further treatment or modification of silicon, surface adsorption of electron-withdrawing (donating) species like $NO_2$ ($NH_3$) decreases (increases) the overall resistance of the p-type Si devices. A significant distinction of the this vapor delivery system is that it can mix the analytes of interest with a calibrated amount of humidified air as opposed to dry $N_2$ to simulate a real-world testing environment. Sensor testing in humidified air is a crucial step towards real-world implementation because SiNWs are highly sensitive to water vapors.

Figure 4A:
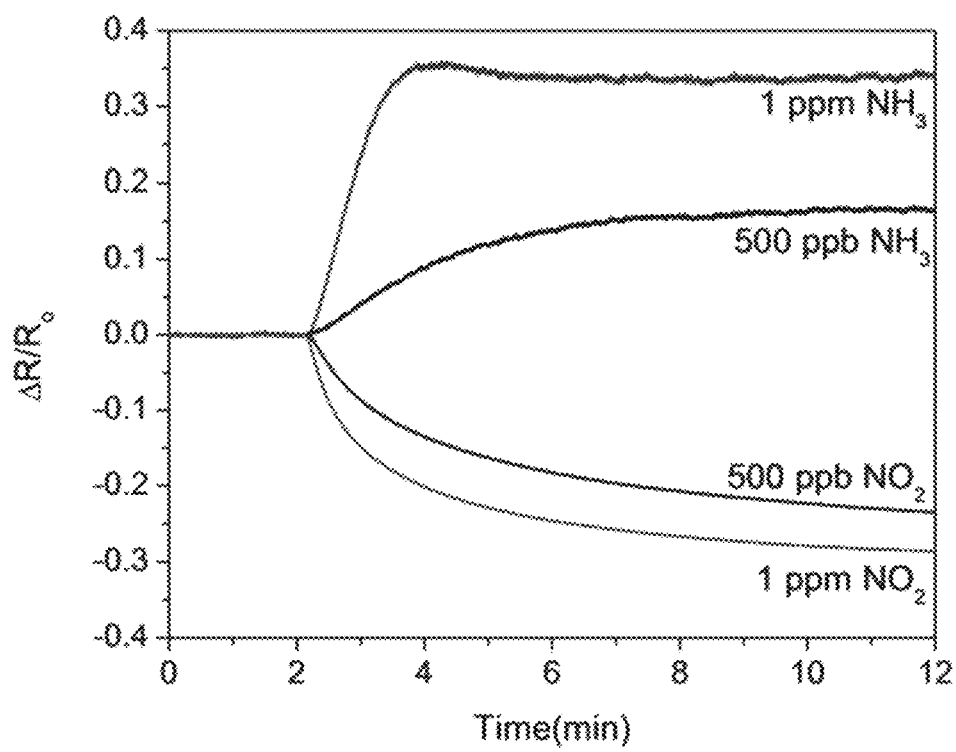
FIGS. 4A-B show sensor response to various concentrations of $NO_2$ and $NH_3$ following 2 min of clean air.
Figure 4B:
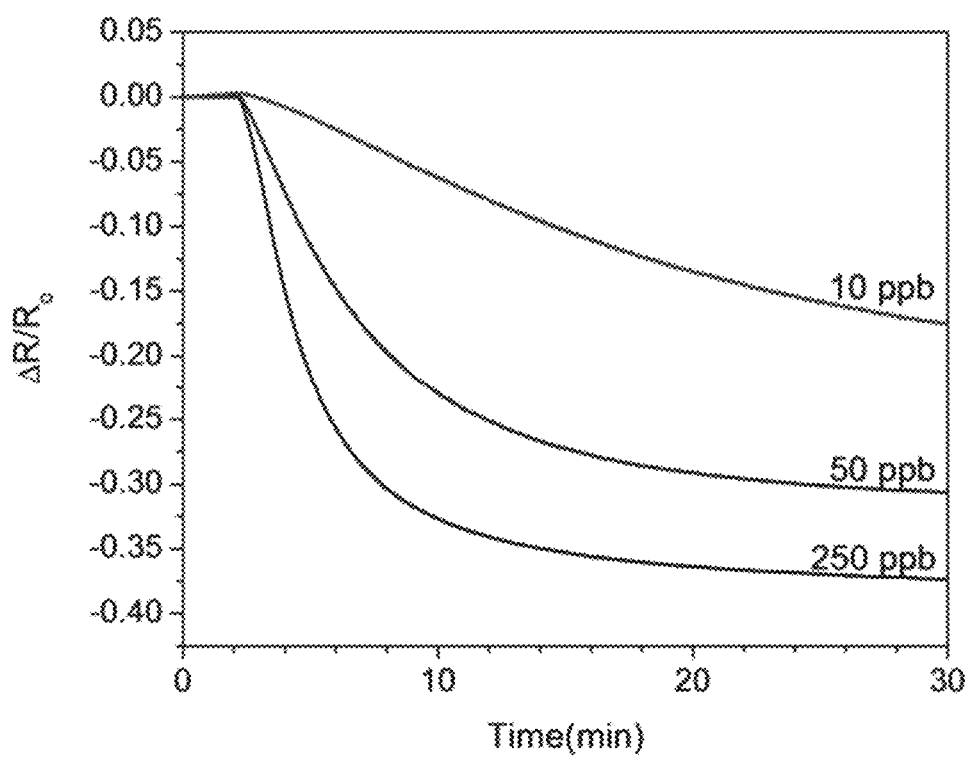

The prototype sensors were tested for response to varying concentrations of $NO_2$ or $NH_3$ at a controlled temperature of 40° C. and relative humidity of ~30%. The change in resistance was determined by holding a constant current of 10 μA while recording voltage with a voltmeter. Sensor response was plotted as the change in resistance divided by the baseline resistance ($\Delta R/R_0$), without any filtering or smoothing of the raw, real-time data. FIG. 4A shows the response of the prototype sensors to 1 ppm and 500 ppb of $NO_2$ and $NH_3$ in humidified air, respectively. As expected, total device resistance increased when exposed to $NH_3$ and decreased upon exposure to $NO_2$. The response reached saturation within a few minutes likely due to the PTE while the massively parallel nanowire configuration resulted in a very low noise profile. Humidified air adversely affects $NO_2/NH_3$ detection capabilities in metal oxide (Starke et al., *Sensors and Actuators B,* 2002, 239-45) and carbon nanotube (Zhang et al., *Nanotechnology* 20 (2009) 255501) sensors. However, water appears to improve the sensor response at very low analyte concentrations. For detection at lower concentrations, the humidity level in the testing chamber was reduced to <10% RH. Sensor response following 30 min of exposure to 250, 50, and 10 ppb of $NO_2$ is shown in FIG. 4B. For the lowest concentration level of 10 ppb, the sensor exhibited an 18% drop in resistance; 10 ppb sensitivity to $NO_2$ is among the lowest ever reported for a SiNW-based sensor and is far below various international and national requirement standards for annual $NO_2$ exposure (Belanger et al., *Am. J. Resp. Crit. Care Med.* 173 (2006) 297-303).

Figure 5A:
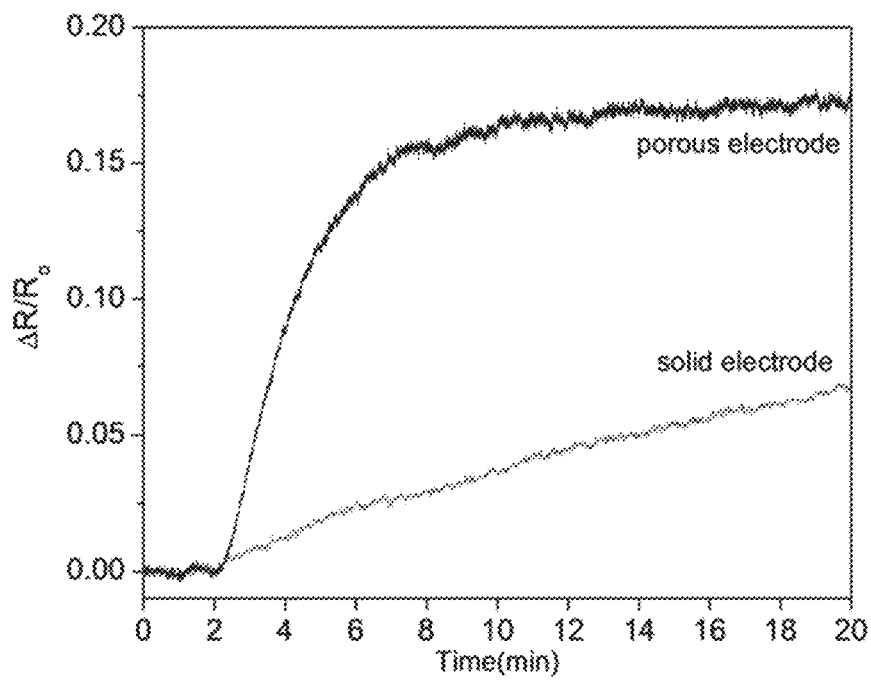
FIG. 5A shows PTE sensor and solid electrode sensor response to 500 ppb of $NH_3$ at ~30% RH.
Figure 5B:
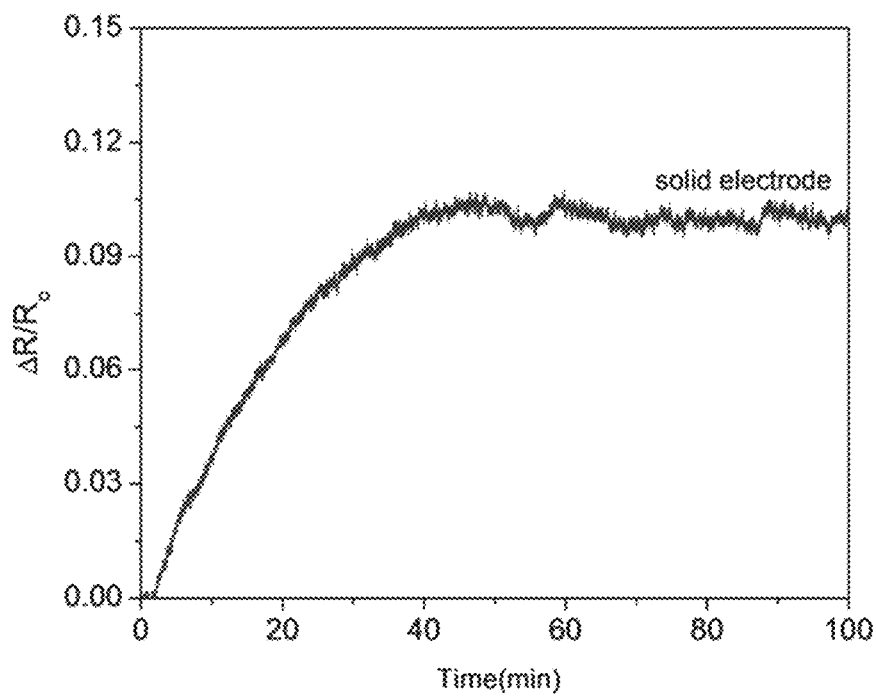
FIG. 5B shows the delayed saturation response of the solid electrode sensor.

The effect of the PTE on sensing performance was investigated by omitting the second nanosphere deposition step in the fabrication process to produce sensors with solid, non-porous electrodes. The devices with and without holes in the electrode layer were identical in all other aspects. The sensing response of both types of devices to 500 ppb of $NH_3$ is shown in FIGS. 5A-B. Both sensors reached similar saturation levels over time, but the PTE sensors, represented by the top line, reached this level in approximately 6 min. The non-porous variety, on the other hand, required almost 1 h to reach saturation. The response to $NO_2$ was also faster for the PTE sensors, albeit not as pronounced as with $NH_3$. This difference is explained by the parallel electrical configuration of the nanowires and the different resistance changes induced by the interacting molecules. $NH_3$ induces a resistance increase, so most of the nanowires must change for a large overall response by the array. In contrast, $NO_2$ decreases the individual nanowire resistance, so only a few nanowires can cause a large change in resistance for the entire array. For all detection schemes, but in particular for those resulting in increased nanowire resistance, the holes in the top electrode layer significantly improve detection response by allowing the analytes to flow directly through the electrode layer to quickly interact with all the nanowires in the array. The relative sensitivity to analyte electronegativity could be reversed by fabricating the nanowires from n-doped Si.

In another experiment, a total of six sensors from a single batch were tested. The sensors were initially exposed to clean air for 2 min, followed by exposure to either ammonia or nitrogen dioxide for 8 min. An adsorption-based sensor should follow a Langmuir adsorption model and be mass-transport limited; thus, the resistance should change asymptotically (Washburn et al., *Anal. Chem.* 81 (2009) 9499-9506; Washburn et al., *Anal. Chem.* 82 (2011) 69-72; Eddowes et al., *Biosensors* 3 (1987) 1-15; Bunimovich et al., *J. Am. Chem. Soc.* 128 (2006) 16323-16331). The 8 min exposure time was used to determine the full rise time of the sensor response for both ammonia and nitrogen dioxide.

Figure 6:
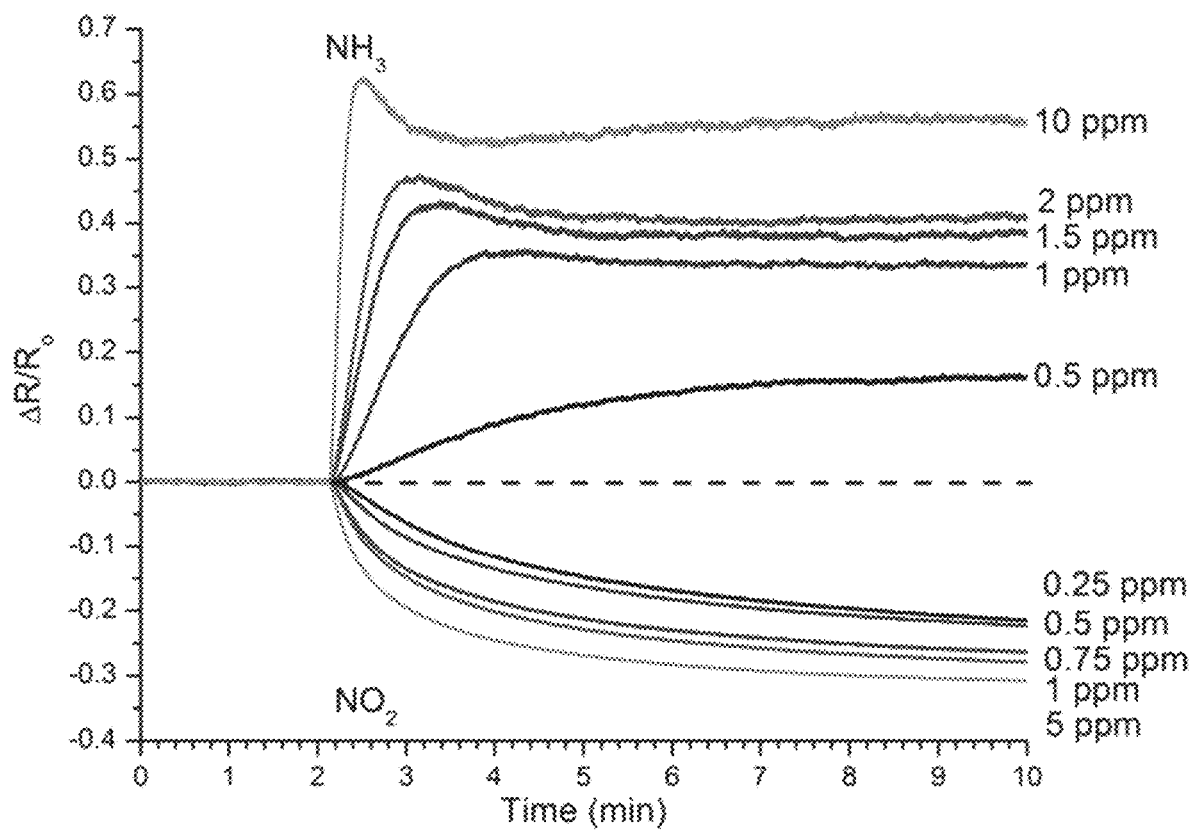
FIG. 6 shows sensor response to ammonia and nitrogen dioxide at various concentrations. The dashed line is an extension of the baseline for comparison.

The responses to ammonia or nitrogen dioxide at 40° C. at different concentrations are shown in FIG. 6. The data presented are from one representative sensor; results from additional sensors were generally consistent. The slight elevation in temperature eliminated temperature-induced fluctuations in sensor response. The concentrations of ammonia and nitrogen dioxide ranged from 250 ppb to 10 ppm. From FIG. 6, as noted and expected, the resistance increased for ammonia and decreased for nitrogen dioxide. The response saturated (leveled off) at approximately 10 min run time (8 min exposure time) for both analytes, regardless of concentration. However, the sensor needed at least 1 h of clean air exposure to partially desorb the analyte from the nanowire surfaces and return to a stable, flat baseline at 40° C. (data not shown). Because of irreversible adsorption of analytes on the nanowires, the baseline never fully recovered to its original, pre-exposure resistance but reached a new equilibrium resistance and over time the sensor lost sensitivity. The incomplete desorption of analyte from the nanowire surface during exposure limited the number of exposures and prevented replicate measurements for each concentration of ammonia or nitrogen dioxide. The recovery and lifetime can probably be improved with a higher operating temperature since adsorption/desorption is temperature dependent but is a trade-off with sensitivity and requires additional optimization. Thermal desorption of the analyte could easily be accomplished to regenerate the sensor by passing an electrical current through the wires, resulting in Joule heating and a rise in their temperature.

FIG. 6 shows the resistance change for exposure to 10 ppm ammonia, including a maximum during the initial exposure. This initial maximum is only observed at relatively high ammonia concentrations and is most pronounced at 10 ppm. No initial maximum is observed for nitrogen dioxide at any concentration, which suggests that it is analyte specific. For example, ammonia and humidified air could react to form ammonium hydroxide. Alternatively, ammonia may dissociate to $NH_2$ and H on the silicon surface, as has been observed at room temperature in ultra-high vacuum (Bozso et al., *Phys. Rev. Lett* 57 (1986) 1185; Dillon, *J. Vac. Sci. Technol., A* 9 (1991) 2222). Dissociation would change the chemistry or restructure the silicon nanowire surface and could make the remaining surface less reactive. While the source of the initial maximum has not been definitively identified, its presence does not hinder additional analysis of the silicon nanowire-based sensor's overall response and performance.

FIG. 6 shows the rapid response as a sharp increase in resistance after exposure to ammonia following a 2 min exposure to clean air. The seconds-to-minutes saturation response of the silicon nanowire-based sensor is remarkable because the sensor is at near-room-temperature and humidified air is used as the carrier, as opposed to dry air or an inert gas. A direct comparison between sensors with porous and solid top electrodes confirmed that the porosity enables the rapid response. Modeling and simulations of the conical sample chamber (data not shown) indicate a uniform vapor front is delivered through the PTE over the entire sensor surface, thereby reducing the diffusion time for the analyte molecules to traverse the wire array.

The signal-to-noise ratio of the silicon nanowire-based sensor is markedly improved over comparable nanotube and nanowire-based sensors (Peng et al., *Appl. Phys. Lett.* 95 (2009) 243112; Lee et al., *J. Phys. Chem. B* 110 (2006) 11055-11061; Snow et al., *Chem. Soc. Rev.* 35 (2006) 790-798; Snow et al., *Nano Lett.* 5 (2005) 2414-2417; Robinson et al., *Nano Lett.* 8 (2008) 3137-3140). The signal-to-noise ratio was approximately 1000:1 for both of the analytes tested in humidified, near-room temperature air (FIG. 6). This result was obtained at a sample rate of 10 Hz and required no post-acquisition smoothing, filtering, or background subtraction. The excellent analyte response and minimal background humidity response are attributable to the PTE and the fact that every nanowire in the array is in electrical contact with both the top and bottom electrodes. Other vertically aligned nanowire-based sensors have relatively small electrodes in contact with only a fraction of the unordered nanowires, so only a small number of the nanowires act as sensing elements (Peng et al., *Appl. Phys. Lett.* 95 (2009) 243112). The PTE in the present sensor ensures that every nanowire is a sensing element in a massively parallel array that minimizes noise sources sensitive to the number of charge carriers, e.g., 1/f noise. Shot noise at the interface between the nanowires and the PTE was further minimized by removing the native oxide layer from the tips of the nanowires.

Figure 7:
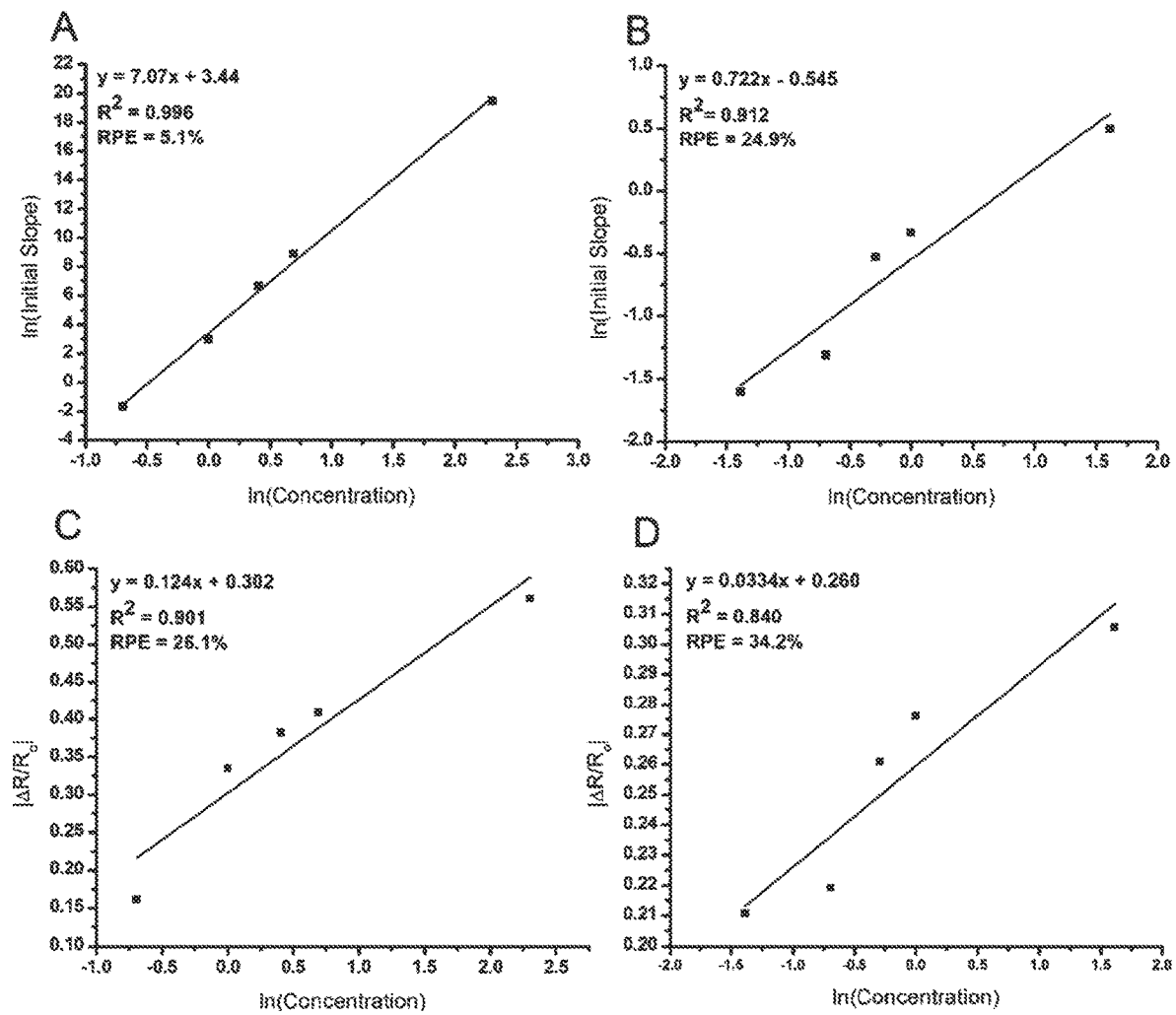
FIG. 7 shows the calibration curves for (A) ammonia and (B) nitrogen dioxide using an initial slope-based method and the calibration curves for (C) ammonia and (D) nitrogen dioxide using a fixed-time point method with $|\Delta R/R_0|_{saturation}$.

The initial slope method has been effectively used for adsorption-based sensors as a means of obtaining quantitative information, but notably in the liquid phase and for non-nanowire-based sensors (Washburn et al., *Anal. Chem.* 81 (2009) 9499-9506; Washburn et al., *Anal. Chem.* 82 (2010) 69-72; Eddowes, *Biosensors* 3 (1987) 1-15). An initial slope method allows for shorter sampling times without the need to achieve saturation and can yield a more linear calibration curve over a larger dynamic range. The sensor response at each concentration of ammonia and nitrogen dioxide in FIG. 6 was fitted to a single exponential function ($y=Ae^{-t/r}+y_0$). The slope at t=0, which is the time when the valve is switched to the analyte line, is simply, A/r. FIG. 7, panels A and B show calibration curves for ammonia and nitrogen dioxide, respectively, where the initial slope (A/r) is plotted versus concentration on a ln—ln scale.

A fixed-time point method using $|\Delta R/R_0|_{saturation}$, where $|\Delta R/R_0|_{saturation}$ is the normalized response at 10 min run time, was also used to establish calibration curves for comparison (FIG. 7, panels C and D). The $R^2$ is 0.996 and 0.912 for the initial slope method and 0.711 and 0.807 for the fixed-time point method. The relative prediction error (RPE), which is the average of the error associated with each calculated concentration in the calibration curve, for ammonia and nitrogen dioxide is 5.1% and 24.9% for the initial slope method compared to 49.0% and 40.3% for the fixed time point method, respectively. Under mass-transport limited conditions, the initial slope exhibits a power law dependence that correlates better with concentration than a fixed-time point at saturation. The ammonia calibration curve is reasonable considering the curve fitting does not explicitly model the initial maximum observed at higher concentrations, but the nitrogen dioxide calibration curve can still be improved, perhaps with a better fitting model than a single exponential.

The initial slope method provides a better correlation to concentration than the fixed-time point method because it eliminates sensor saturation. This not only reduces sampling times and makes the sensor more applicable to real-world environments but also improves sensor recovery and lifetime by limiting the amount of material needed for quantitation and the amount that must be desorbed to regenerate the sensor.

A preconcentrator was also made. A self-assembled layer of polystyrene beads was spin coated onto the silicon substrate, and reactive ion etching was used to reduce the bead size, defining the final nanowire diameter and spacing. A 25 nm gold metal layer was deposited, and the beads were then removed via solvent. The polystyrene beads act as a nanomask, leaving the gold film pierced by an array of holes equal in size to the beads. Next, metal-assisted chemical etching (MACE) was used to create the highly ordered nanowire array. Briefly, the sample was immersed in a solution of hydrofluoric acid (HF) and hydrogen peroxide, whereupon a redox reaction occurred at the interface between the gold and the silicon. The silicon oxidized and the oxide was removed by the HF. As a result, the gold film effectively "sinks" into the Si wafer; wherever there is a hole in the film, a Si nanowire is formed. Fabrication was completed by the deposition of a $2^{nd}$ porous gold electrode on top of the array, which allows vapor to penetrate into the array in a top down fashion. The porous top electrode allows one to pass a current and heat the SiNWs while also allowing analytes to pass quickly into the array during sampling and out of the array during desorption.

The temperature-dependent shift in the Si Raman single phonon line was used to estimate the temperature of the SiNWs as a function of applied current. The relationship between the one-phonon Raman peak location and temperature rise in Si is approximately linear from room temperature to 600K (Balkanski et al, "Anarmonic Effects in Light Scattering Due to Optical Phonons in Silicon," *Phys. Rev. B.* Vol. 28, pp. 1928-1934, 1983). At room temperature, the one-phonon Raman peak occurs at ~520 $cm^{-1}$. For every 1 K increase in temperature, the Raman peak shift decreases by about 0.02 $cm^{-1}$. It should also be noted the Raman peak broadens with temperature.

Figure 8:
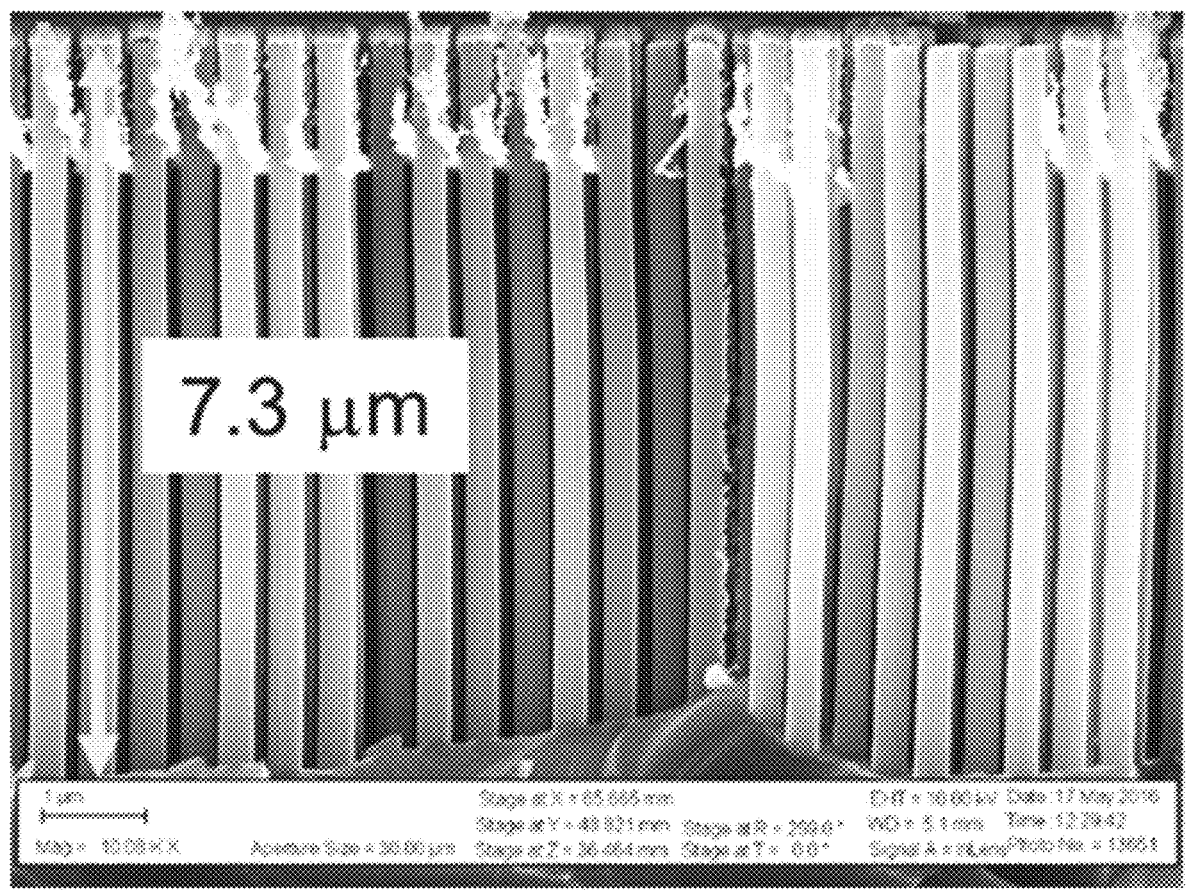
FIG. 8 shows an SEM side view of SiNW array.
Figure 9:
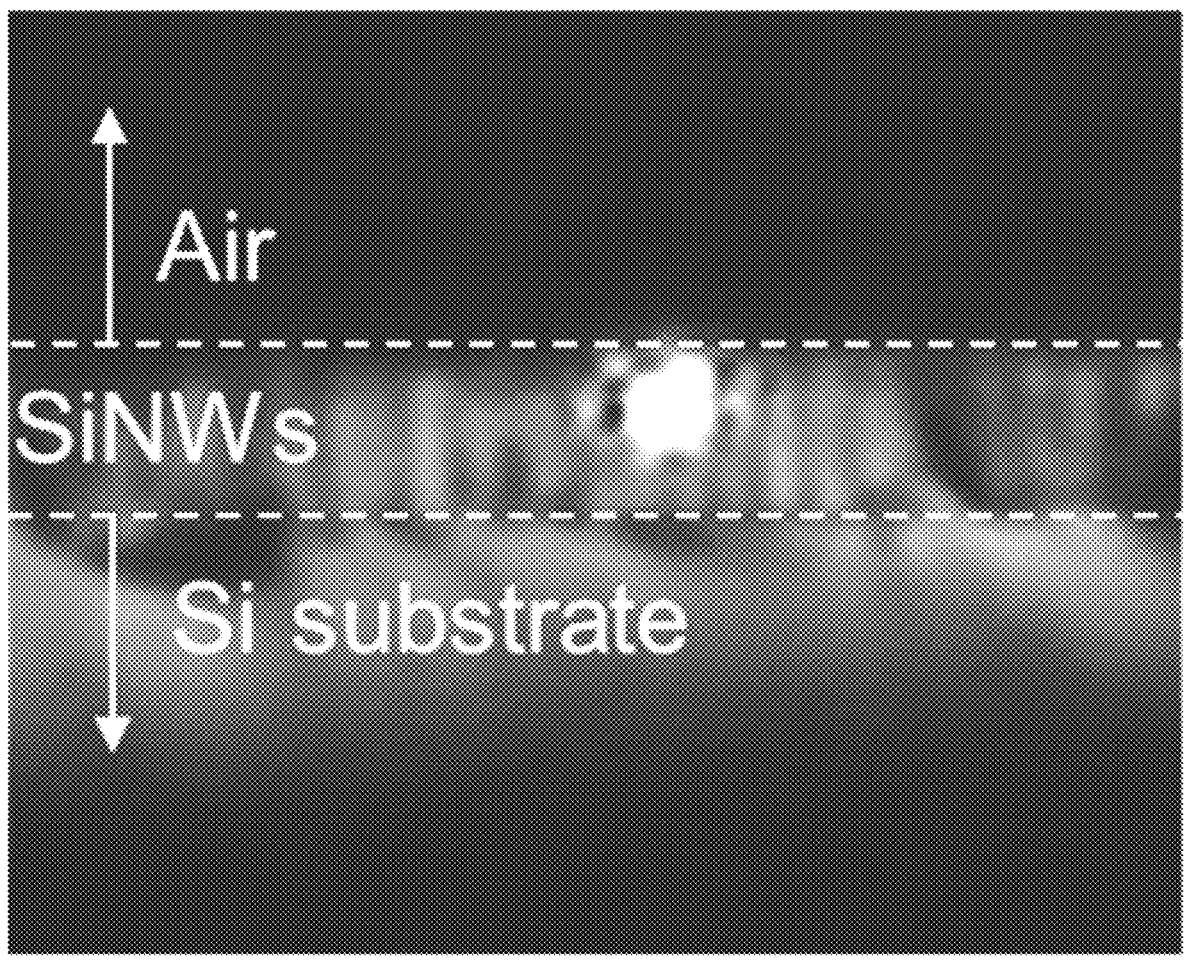
FIG. 9 shows an optical side view of array. The bright spot indicates the Raman laser.
Figure 10:
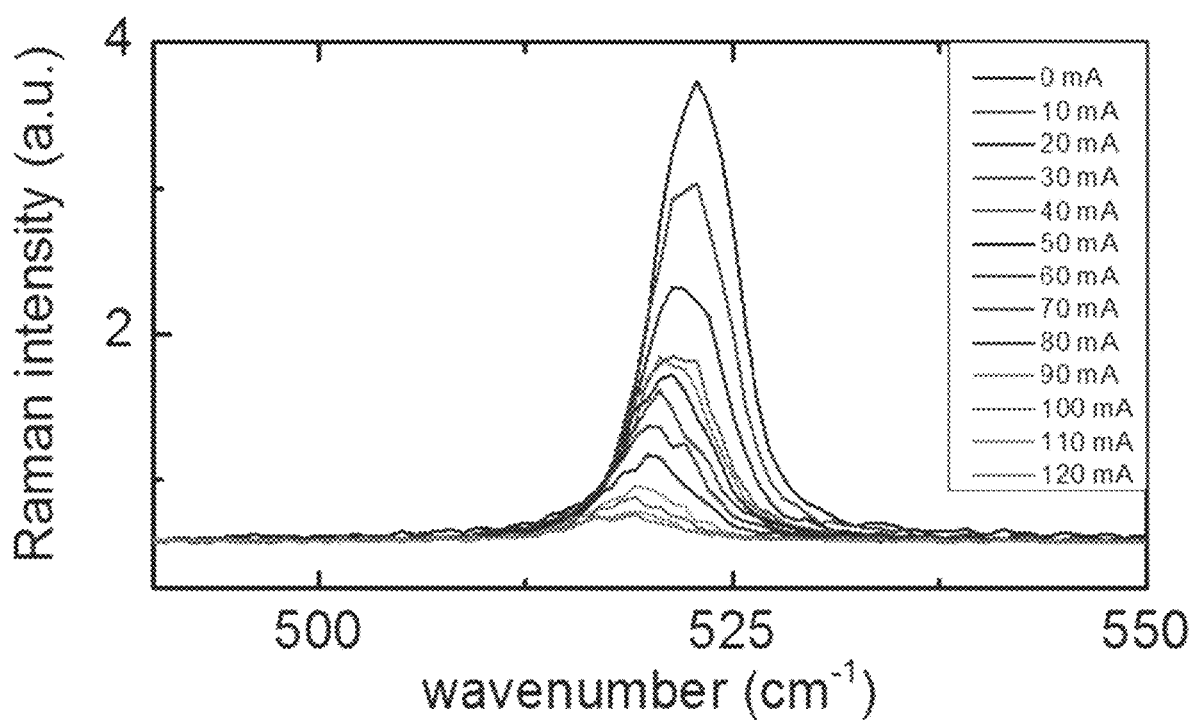
FIG. 10 shows the Raman spectra as a function of applied current.

FIG. 8 shows an SEM side view of the SiNW array. FIG. 9 shows an optical image of the array. The Si substrate is located at the bottom of the image, and the SiNWs are located between the white dashed lines. The Raman spectrum as a function of current was collected from a few SiNWs located the laser focus spot (bright spot in the middle of the image). Current was run through the SiNWs by applying a voltage between the porous top electrode and the Si substrate. The Raman spectrum for applied currents ranging from 0 mA up to 120 mA is shown in FIG. 10. Note that as the current increased, the Raman peak red-shifted and broadened, indicating a rise in the SiNW temperature. The spectral intensity also decreased with increasing current. It is known that the Raman peak intensity decreases with temperature, but part of the decrease observed may also be due to thermal drift.

Figure 11:
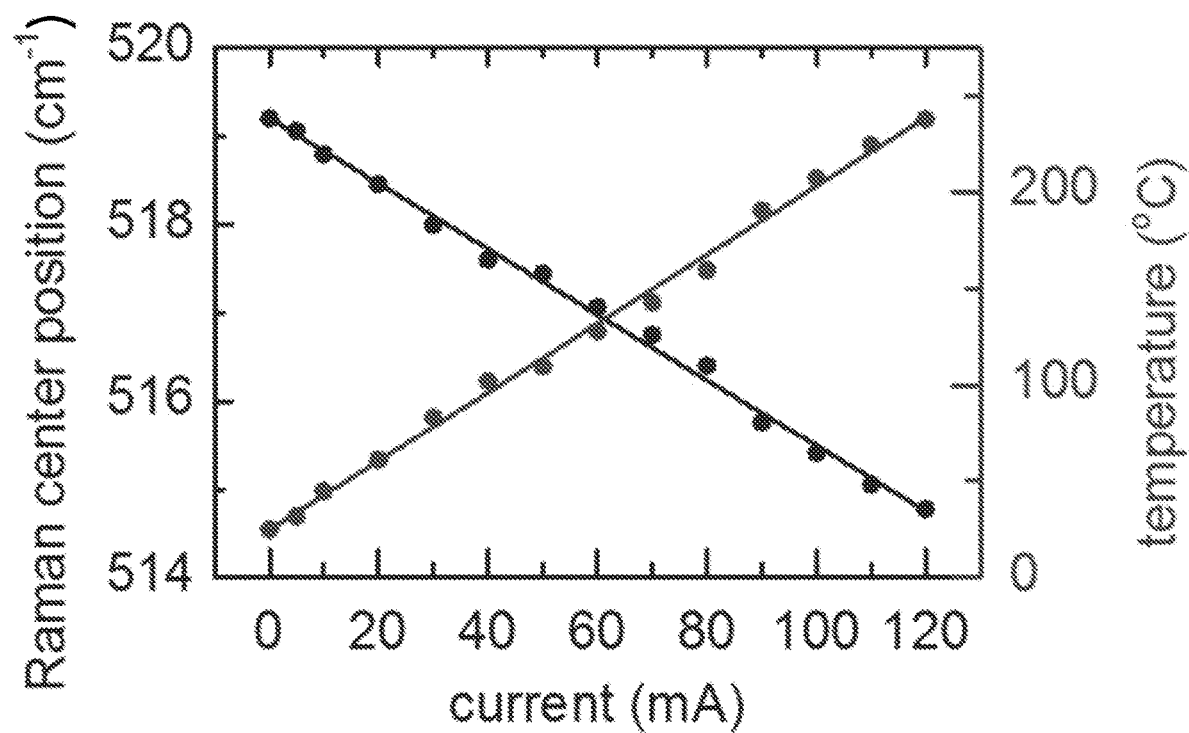
FIG. 11 shows the temperature versus current relationship.

Each Raman FIG. 10 was fitted with a Gaussian line shape. The center wavenumber of the Gaussian fit is plotted in FIG. 11 as a function of applied current. A linear fit of the Raman peak center wavenumber vs. current yields a slope of −0.037 $cm^{-1}$/mA. To convert the Raman center position to SiNW temperature, the following equation was used:

$$\text{temperature}=(R_{RT}-R(I))/0.02 \text{ cm}^{-1}/°C.+22° C.$$

where $R_{RT}$ is the Raman center position at room temperature (i.e., applied current=0 mA) and R(I) is the Raman center position at an applied current of I. A room temperature of 22° C. was assumed. A linear fit of the temperature vs. current yields a slope of 1.78° C./mA.

Trace 2,4-DNT vapors were delivered to SiNW arrays using a custom made vapor handling system. Briefly, a calibrated permeation tube of 2,4-DNT was placed in a permeation oven and operated per manufacturers specifications to produce a nominal mass flux of 2,4-DNT per unit time. The volume flow rate of air through the permeation oven was 1 L/min. The nominal vapor concentration was attenuated by controlled flow of purified air, allowing for total flow rates of 3.5 to 21 L/min or vapor concentration range from 28.4 to 4.7 $ppb_v$.

The desorption of 2,4-DNT from the array was detected using an Agilent 5976 mass selective detector (MSD). Briefly, the sample chamber contained a stainless steel base and a ZIF socket to which the SiNW array, mounted on a pin grid array chip, was connected. A Plexiglas top sealed directly to the pin grid array chip. Multiple access ports allowed the introduction and exit of 2,4-DNT vapor, and access to the MSD by a heated capillary transfer line.

Arrays were evaluated by delivering a known concentration of 2,4-DNT vapor to the array at a particular flow rate and duration, resulting in the delivery of a nominal mass of 2,4-DNT to the sample chamber. After sample loading, desorption programs were initiated using a custom Lab VIEW program controlling a Keithley 2602A SourceMeter.

Figure 12:
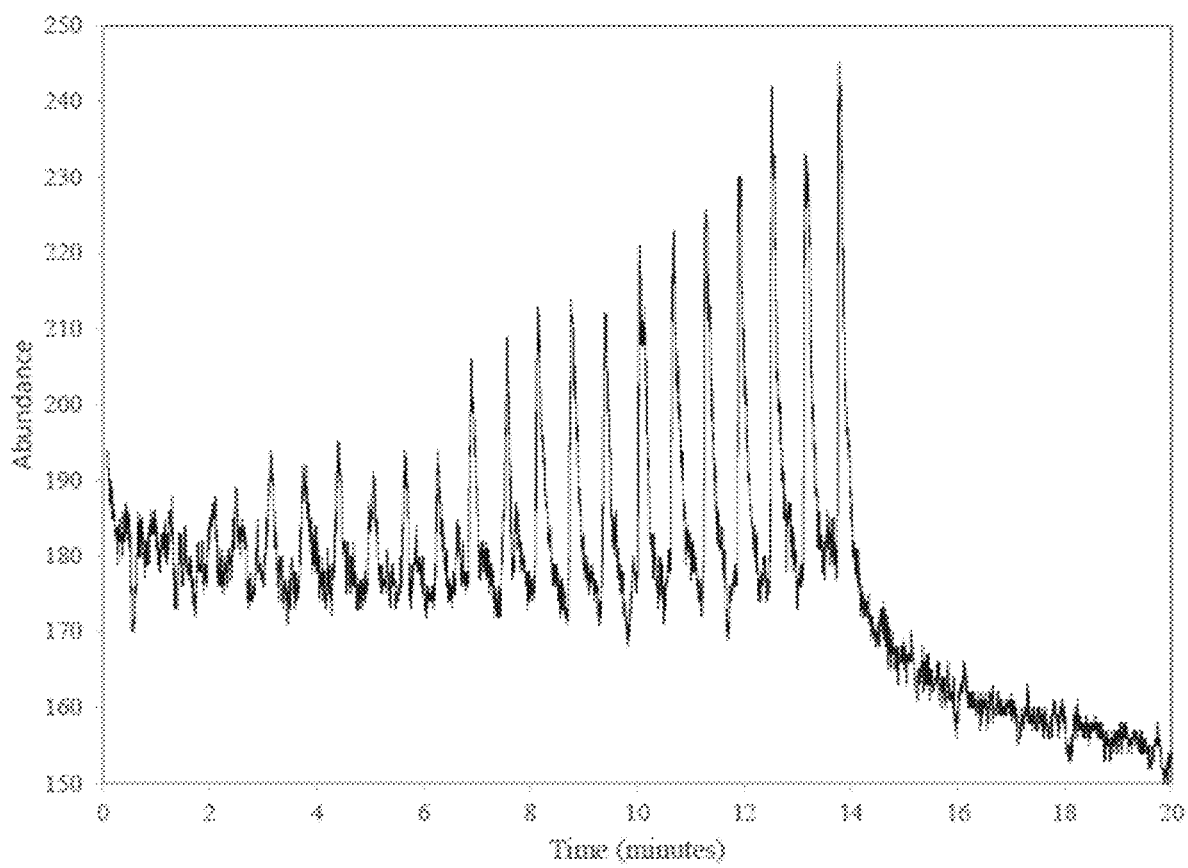
FIG. 12 shows current titration desorption beginning at 10 mAmps to 200 mAmps, at 10 mAmp increments (200 mAmp is repeated once). Current was applied for 8 seconds, with 30 seconds between each application. A 28.4 $ppb_v$ vapor was sampled for 5 minutes at 200 mL/min providing a nominal sample load of 211 ng of 2,4-DNT. Mass selective detection at m/z=77, 89, 123, 165.

A representative desorption "chromatogram" is shown in FIG. 12. In this instance, over 200 ng of 2,4-DNT was delivered to the array. Desorption current was applied, starting with 10 mAmps for 8 seconds, and increased to 200 mAmps at 30 second intervals. The peak area of 2,4-DNT plateaued at approximately 160 mAmps. The concentration of 2,4-DNT vapor, estimated from the chromatogram, was in excess of 1000 ppb.

This work demonstrates the successful preconcentration and desorption of 2,4-DNT from SiNW arrays. The array's large surface array enables analyte adsorption on the surface without a stationary phase. Rapid desorption occurs when the nanowires are Joule heated by passing a current through them. This work suggests the feasibility of this approach for inclusion as an integrated preconcentration stage for new laboratory and portable analytical devices.

Figure 13:
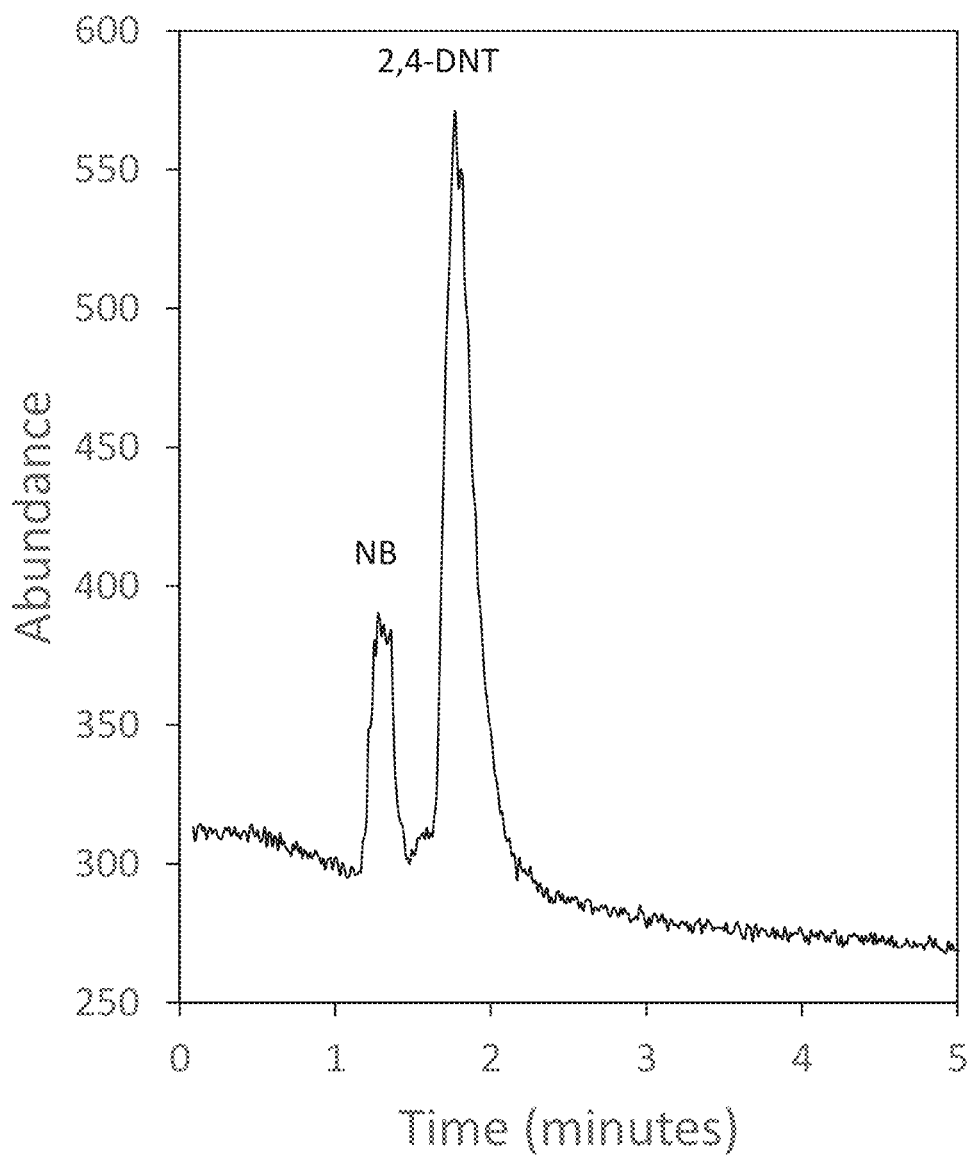
FIG. 13 shows a separation of nitrobenzene (NB) and 2,4-DNT.

In a similar fashion, a mixture of nitrobenzene (NB) and 2,4-DNT was delivered to the Si NW array. Nominal vapor concentrations were 30 $ppb_v$ and 4.5 $ppb_v$, respectively. Sample flow rates and time were such that the nominal mass load to the array was 30 ng of NB and 7 ng of 2,4-DNT. At t=1 minute, desorption current was applied for approximately 10 seconds, resulting in the desorption of NB and 2,4-DNT from the array. Results are depicted in FIG. 13.

Figure 14:
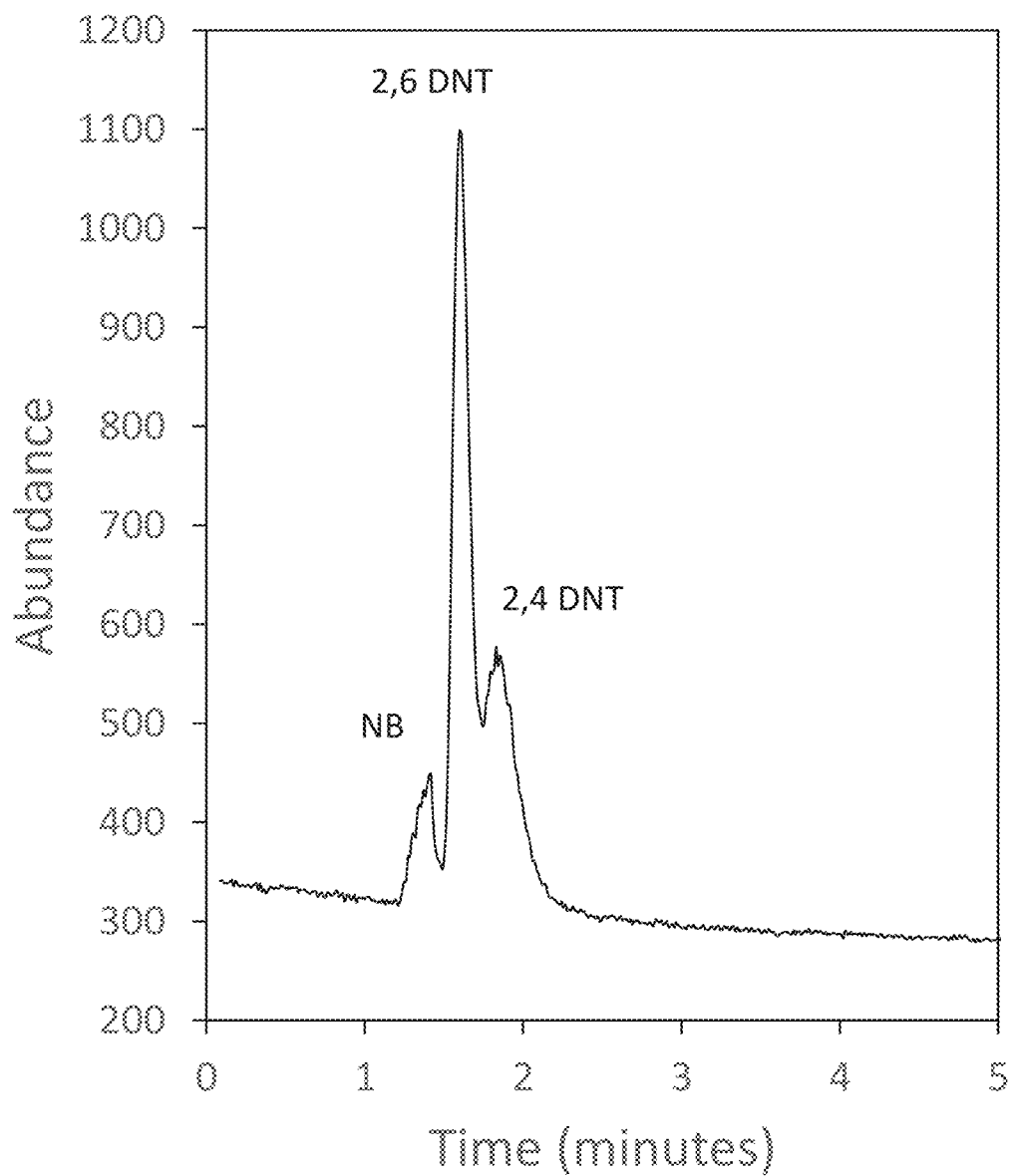
FIG. 14 shows a separation of nitrobenzene, 2,6-DNT, and 2,4-DNT.

In a similar fashion, a mixture of nitrobenzene (NB), 2,6-DNT, and 2,4-DNT was delivered to the Si NW array. Nominal vapor concentrations were 30 $ppb_v$, 9.9 $ppb_v$ and 4.5 $ppb_v$, respectively. Sample flow rates and time were such that the nominal mass load to the array was 30 ng of NB, 15 ng for 2,6-DNT, and 7 ng of 2,4-DNT. At t=1 minute, desorption current was applied for approximately 10 seconds resulting in the desorption of the three components from the array. Results are depicted in FIG. 14.

Figure 15:
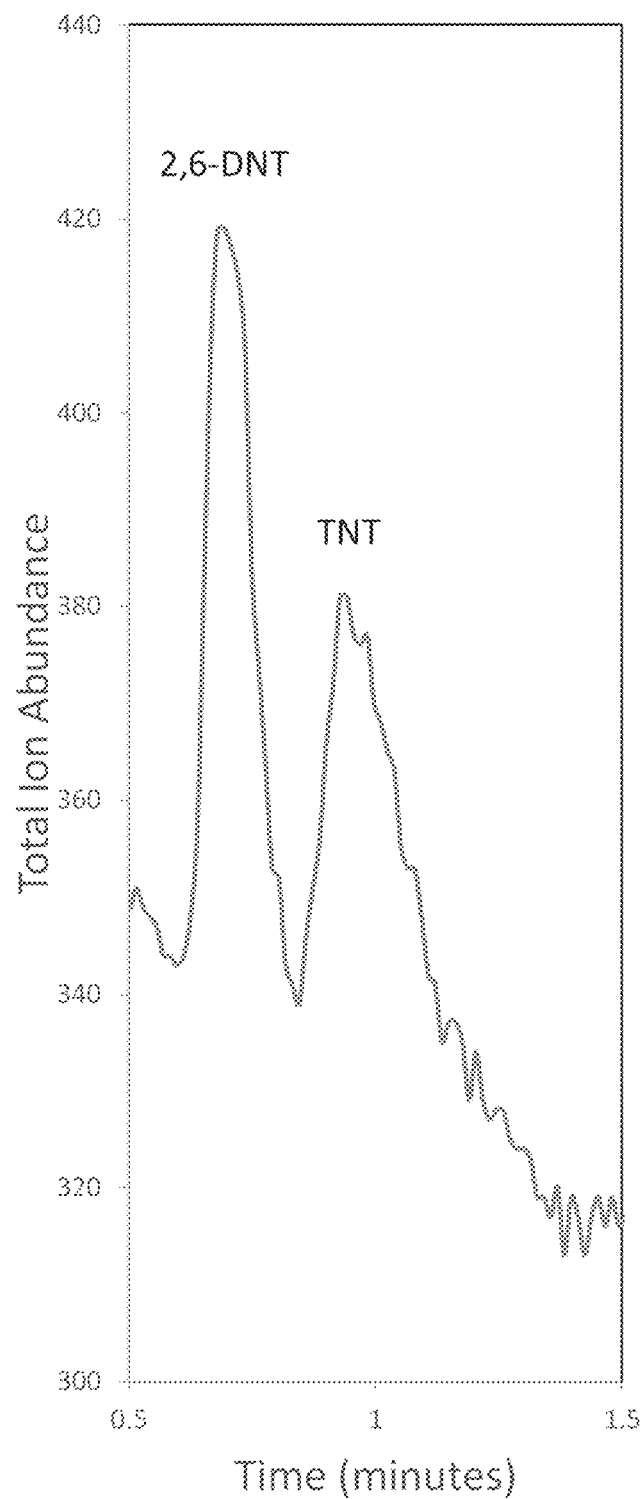
FIG. 15 shows a separation of 2,6-DNT and TNT.

In a similar fashion, a mixture of 2,6-DNT and TNT was delivered to the Si NW array. Nominal vapor concentrations were 10 $ppb_v$, and 8 $ppb_v$, respectively. Sample flow rates and time were such that the nominal mass load to the array was 60 ng of each analyte. At t=0.5 minute, desorption current was applied for approximately 10 seconds, resulting in the desorption of the two components from the array. Results are depicted in FIG. 15.

Numerous potential applications and device configurations exist, including, but not limited to, 1) the use of a matrix of SiNW arrays with different sorbent materials resulting in the generation of desorption "chromatograms" that vary as a function of analyte affinity to the sorbent material, 2) the use of Si NW to provide meter doses of vapor on demand, by first overloading the Si NW array with sample and briefly heating the array to only deliver a small portion of the adsorbed analyte. This application is suitable for vapor detector calibration.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A method comprising:
   providing a structure comprising:
      a first electrode;
      a plurality of nanowires perpendicular to the first electrode, each nanowire having a first end in contact with the first electrode;
         wherein the nanowires comprise two or more different chemically selective surfaces; and
      a second electrode in contact with a second end of each nanowire;
   exposing the structure to a sample suspected of containing an analyte that can adsorb onto the nanowires; and
   passing an electrical current through the nanowires to heat the nanowires to a temperature at which the analyte will desorb from the nanowires.

2. The method of claim 1, wherein the second electrode comprises perforations.

3. The method of claim 2, wherein the nanowires and the perforations are periodically arranged.

4. The method of claim 1, wherein the nanowires comprise silicon.

5. The method of claim 1, wherein the chemically selective surface is an adsorbing layer, a stationary phase, or a surface functionalization.

6. The method of claim 1, wherein the second electrode is a continuous material.

7. The method of claim 1, wherein the second electrode comprises titanium and gold.

8. The method of claim 1, further comprising:
   detecting any desorbed analyte.

9. The method of claim 8, wherein the detection is by mass spectroscopy, ion mobility spectrometry, change in fluorescence intensity of a fluorescent probe, change in resonance of a cantilever, change in frequency of a cantilever, change in resistance of a chemiresistor, or detection by a nanowire array.

10. The method of claim 8, further comprising:
    passing the desorbed analyte through a gas chromatograph before detecting the desorbed analyte.

11. The method of claim 1, wherein there are no electrodes between the sides of the nanowires.

12. An apparatus comprising:
    a structure comprising:
       a first electrode;
       a plurality of nanowires perpendicular to the first electrode, each nanowire having a first end in contact with the first electrode;
          wherein the nanowires comprise two or more different chemically selective surfaces; and
       a second electrode in contact with a second end of each nanowire;
    a current source electrically connected to the first electrode and the second electrode; and
    a detector configured to detect an analyte that may be desorbed from the nanowires.

13. The apparatus of claim 12, wherein the chemically selective surface is an adsorbing layer, a stationary phase, or a surface functionalization.

14. The apparatus of claim 12, wherein the detector is a mass spectrograph, an ion mobility spectrograph, a fluorescence probe, a microcantilevers, a chemiresistor, or a nanowire array.

15. The apparatus of claim 12, further comprising:
a gas chromatograph configured to pass the analyte from the nanowires to the detector.

16. The apparatus of claim 12, wherein there are no electrodes between the sides of the nanowires.

\* \* \* \* \*